(12) United States Patent
Lukacs et al.

(10) Patent No.: US 10,328,463 B2
(45) Date of Patent: Jun. 25, 2019

(54) ULTRASONIC TRANSDUCER WITH BACKING HAVING SPATIALLY SEGMENTED SURFACE

(71) Applicant: SUNNYBROOK HEALTH SCIENCES CENTRE, Toronto (CA)

(72) Inventors: Marc Lukacs, Toronto (CA); Brian Courtney, Toronto (CA); Chelsea Munding, Caledonia (CA)

(73) Assignee: SUNNYBROOK HEALTH SCIENCES CENTRE, Toronto (CA)

( * ) Notice: Subject to any disclaimer, the term of this patent is extended or adjusted under 35 U.S.C. 154(b) by 423 days.

(21) Appl. No.: 15/038,569

(22) PCT Filed: Nov. 21, 2014

(86) PCT No.: PCT/CA2014/051111
§ 371 (c)(1),
(2) Date: May 23, 2016

(87) PCT Pub. No.: WO2015/074152
PCT Pub. Date: May 28, 2015

(65) Prior Publication Data
US 2016/0296975 A1 Oct. 13, 2016

Related U.S. Application Data

(60) Provisional application No. 61/907,765, filed on Nov. 22, 2013.

(51) Int. Cl.
*B06B 1/06* (2006.01)
*A61B 8/12* (2006.01)
(Continued)

(52) U.S. Cl.
CPC .............. *B06B 1/0685* (2013.01); *A61B 8/12* (2013.01); *A61B 8/4483* (2013.01);
(Continued)

(58) Field of Classification Search
CPC ....... B06B 1/0685; B06B 1/0622; A61B 8/12; A61B 8/4483; G01D 5/48; G01N 29/36; G10K 11/002
(Continued)

(56) References Cited

U.S. PATENT DOCUMENTS 5,474,074 A 12/1995 Suorsa et al.
5,486,734 A 1/1996 Seyed-Bolorforosh
(Continued)

FOREIGN PATENT DOCUMENTS

DE 904955 C 2/1954
EP 2659987 6/2013
(Continued)

OTHER PUBLICATIONS

Kamal Raj Chapagain et al., "Minimizing the bottom reflection in Ultrasonic CMUT Transducer backing using low profile structuring". Ultrasonics Symposium (IUS), 2009 IEEE International, IEEE, Piscataway, NJ, USA. Sep. 20, 2009 pp. 430-433.
(Continued)

*Primary Examiner* — Thomas M Dougherty
(74) *Attorney, Agent, or Firm* — Hill & Schumacher

(57) ABSTRACT

Methods and devices are provided for suppressing reverberations within an ultrasound transducer with a backing whereby the backing may not sufficiently attenuate the acoustic energy by means of acoustic absorption and scattering alone. At least a portion of a surface of the backing is segmented into a plurality of levels defined by surface segments. The levels may be are spatially offset so that acoustic reflections from the segmented surface are spread out in time, thereby decreasing the net amplitude of the internally reflected waves as they interact with the piezoelectric layer. Adjacent (neighboring) levels may be spatially offset by a longitudinal distance equaling approximately an
(Continued)

odd number multiple of a quarter of an operational wavelength of the transducer, so that destructive interference occurs from acoustic waves reflected from adjacent levels. Various example configurations of segmented surfaces are described, and methods for selecting a profile of a segmented surface are provided.

23 Claims, 19 Drawing Sheets

(51) Int. Cl.
    *G01N 29/36*     (2006.01)
    *A61B 8/00*     (2006.01)
    *G01D 5/48*     (2006.01)
    *G10K 11/00*     (2006.01)
    *G01S 15/89*     (2006.01)

(52) U.S. Cl.
    CPC ............ *B06B 1/0622* (2013.01); *G01D 5/48* (2013.01); *G01N 29/36* (2013.01); *G10K 11/002* (2013.01); *G01S 15/8909* (2013.01)

(58) Field of Classification Search
    USPC .................. 310/322, 326, 327, 334, 309
    See application file for complete search history.

(56) References Cited

U.S. PATENT DOCUMENTS

| | | |
|---|---|---|
| 6,792,656 B2 | 9/2004 | Shimoe et al. |
| 8,466,605 B2 | 6/2013 | Kushculey et al. |
| 9,857,457 B2 * | 1/2018 | Chowdhury .............. G01S 7/52 |
| 2005/0236937 A1 * | 10/2005 | Khuri-Yakub ........ B06B 1/0292 |
| | | 310/334 |
| 2012/0013218 A1 | 1/2012 | Huang |

FOREIGN PATENT DOCUMENTS

| | | |
|---|---|---|
| JP | 59-218097 | 12/1984 |
| JP | 07-322394 | 12/1995 |
| JP | 2013160685 | 8/2013 |
| WO | 2005104210 | 11/2005 |

OTHER PUBLICATIONS

Kamal Raj Chapagain et al: "Measurement of the added specular reflection attenuation by using a grooved bottom surface in the backing of CMUTs", Ultrasonics Symposium (IUS) 2011 IEEE, Oct. 18, 2011 pp. 1004-1007.

Kamal Raj Chapagain et al: "Grooved Backing Structure for CMUTs", IEEE Transactions on Ultrasonics, Ferroelectrics and Frequency Control, IEEE, US, vol. 60 No. 11 Nov. 2013 pp. 2440-2452.

Mir Seyed-Bolorforosh, M.S., Ultrasonic transducer with improved bandwidth using phase shift interference in the backing, Ultrasonics Symposium, 1994. Proceedings., IEEE, 1994.

Written Opinion in PCT Application No. PCT/CA2014/051111, dated Feb. 24, 2015.

International Search Report in PCT Application No. PCT/CA2014/051111, dated Feb. 24, 2015.

* cited by examiner

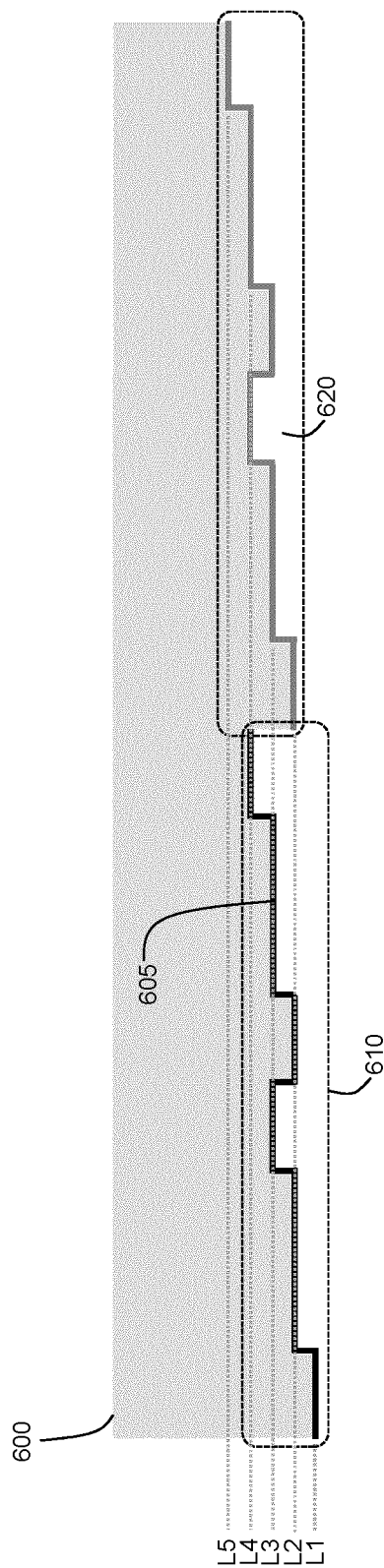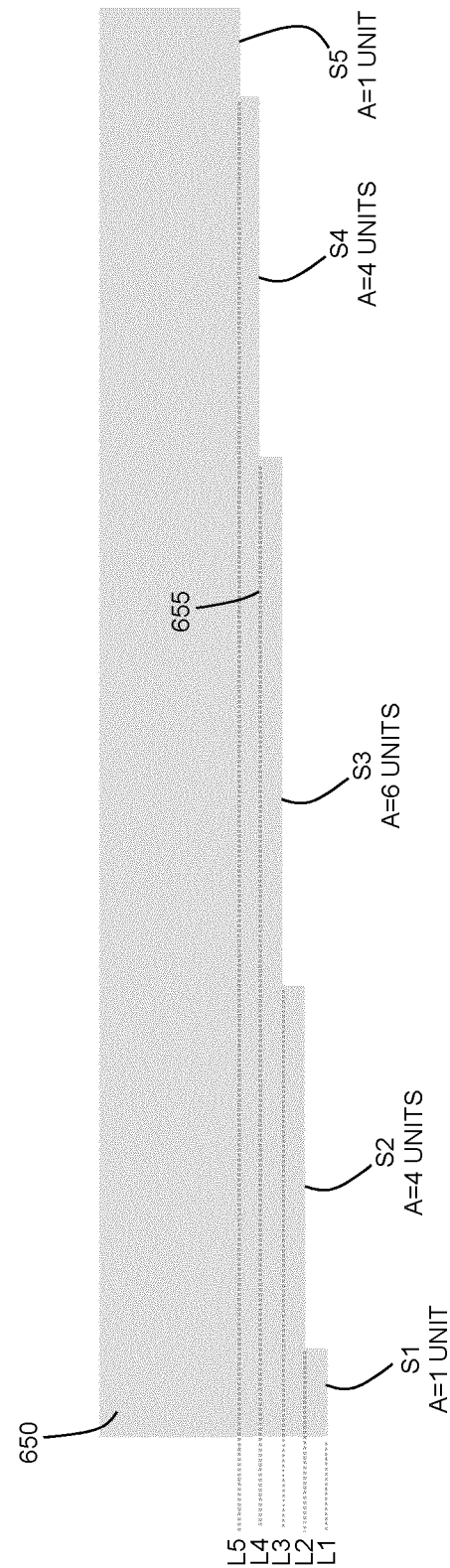

ULTRASONIC TRANSDUCER WITH BACKING HAVING SPATIALLY SEGMENTED SURFACE

CROSS-REFERENCE TO RELATED APPLICATION

This application is a National Phase application claiming the benefit of the international PCT Patent Application No. PCT/CA2014/051111, filed on Nov. 21 2014, in English, which claims priority to U.S. Provisional Application No. 61/907,765, titled "ULTRASONIC TRANSDUCER WITH BACKING HAVING SPATIALLY SEGMENTED SURFACE" and filed on Nov. 22, 2013, the entire contents of which are incorporated herein by reference.

BACKGROUND

The present disclosure relates to ultrasonic transducers. More particularly, the present disclosure relates to ultrasonic imaging and therapeutic devices.

Ultrasonic transducers are employed in a wide array of applications and industries, and are commonly employed in therapeutic and imaging devices.

Typically, an ultrasound transducer includes an active piezoelectric element that is attached to a backing, where the backing is made from a material that prevents spurious acoustic reflections from reaching the active element and interfering with its performance. The backing of an ultrasonic transducer is usually designed to be sufficiently thick to reduce spurious acoustic reflections to levels that are below the electrical noise floor of the system, or at least to levels that allow for an acceptable dynamic range of greyscale in the ultrasound image to differentiate tissue structures and to allow for sufficient contrast between tissue structures of similar acoustic impedance. In many cases, such as handheld ultrasound probes, there is little restriction imposed on the total thickness of a transducer stack, thus allowing the backing layer of the transducer stack to be thick in order to attenuate residual acoustic energy and maintain a short pulse response for the device.

However, if the ultrasonic transducer involves a thin backing layer, such that the acoustic energy that enters into the backing is not completely absorbed or attenuated, then acoustic energy that reflects off of the bottom surface of the backing will return to the piezoelectric layer with a sufficiently large enough amplitude to interfere with the device performance. This time-delayed energy thus generates a secondary signal or reverberation signal within the transducer stack. In transmit mode, the secondary pulse represents a trailing pulse behind the primary pulse propagating into the imaging medium. In receive mode, the secondary pulse creates a potential difference across the electrodes of the active layer that will also be detected by the receive electronics and will be an artifact in any reconstructed image.

For example, such artifacts can be problematic for high axial resolution ultrasound biomedical imaging devices, which require the use of ultrasound transducers that exhibit short time responses with minimal secondary pulses or stack reverberation that will reduce the acoustic dynamic range of the ultrasound image. High frequency clinical ultrasound (generally considered to involve frequencies greater than approximately 5 MHz and in particular greater than 10 MHz), in particular, has found significant use in minimally invasive imaging, such as intracardiac and intravascular applications. For these applications, ultrasound transducers are incorporated into a catheter or other device that can be inserted into a lumen or cavity within the body. This constrains the dimensions of the transducer stack and the volume of backing material that can be included in the transducer design.

A common practice for increasing ultrasound attenuation within a transducer stack, in order to avoid secondary signals and reverberation, is the introduction of scatterers into the backing. Scatterers help to partially break up the spatial coherence of the acoustic energy within the backing medium by inducing spatially variant and localized partial reflections of the propagating acoustic waves. The extent to which the scatterers have an effect in breaking up the coherence will depend on the size of the scatters relative to the wavelength of the propagating wave. For example, in some catheter applications, depending on the desired imaging frequency and the size constraints of the catheter, scattering is not necessarily sufficient to suppress reverberations.

In certain catheter applications in which the transducer is stationary relative to the housing that holds the transducer stack, sloped or angled surfaces, in either the backing or in the housing, may be employed to help to reflect the acoustic energy in different directions such that the path length of the acoustic energy in the backing is effectively increased or that the energy does not return to the piezoelectric active layer or both. However, in other catheter applications in which the transducer may move relative to its surroundings, the backing layer may be the only layer that can be employed to reduce the secondary pulses and reverberation within the transducer stack.

One approach to mitigate the effect of spurious reflections is to use a stack of multiple layers of materials with different acoustic impedance, in effect creating a one-dimensional acoustic grating structure analogous to optical gratings that are, for example, extensively used in fiber optics and telecommunications. This grating structure has a uniform cross section underneath the active area of the transducer stack. Achieving an acoustic grating frequency bandwidth that is wider than the bandwidth of the transducer stack itself requires several layers of several acoustic impedances. This complicates the fabrication of the grating structure and increases the required precision in achieving the desired layer thicknesses. This approach may also require a thickness that exceeds the space constraints of the stack in the first place. Expressed differently, a grating that is small enough to meet the size constraints for a catheter-based imaging transducer may cause the bandwidth of the primary signal/pulse to be substantially reduced, since the functional bandwidth of the grating may become narrower than that of the transducer itself.

SUMMARY

Methods and devices are provided for suppressing reverberations within an ultrasound transducer with a backing whereby the backing may not sufficiently attenuate the acoustic energy by means of acoustic absorption and scattering alone. At least a portion of a surface of the backing is segmented into a plurality of levels defined by surface segments. The levels may be spatially offset so that acoustic reflections from the segmented surface are spread out in time, thereby decreasing the net amplitude of the internally reflected waves as they interact with the piezoelectric layer. Adjacent (neighbouring) levels may be spatially offset by a longitudinal distance equaling approximately an odd number multiple of a quarter of an operational wavelength of the transducer, so that destructive interference occurs from acoustic waves reflected from adjacent levels. Various example configurations of segmented surfaces are described, and methods for selecting a profile of a segmented surface are provided.

Accordingly, in one aspect, there is provided an ultrasonic transducer comprising:

an active layer; and a backing having a proximate surface that is proximate to said active layer, and a further surface therebelow, wherein at least a portion of said further surface is a segmented surface;

wherein said segmented surface comprises a plurality of approximately planar segments, each segment being approximately parallel to said proximate surface; and wherein at least two of the segments are spatially offset in a longitudinal direction that is approximately perpendicular to said proximate surface, thereby defining two or more levels of said segmented surface, such that each level has a different backing thickness associated therewith.

In another aspect, there is provided an ultrasonic array comprising a plurality of such ultrasonic transducers.

A further understanding of the functional and advantageous aspects of the disclosure can be realized by reference to the following detailed description and drawings.

BRIEF DESCRIPTION OF THE DRAWINGS

Embodiments of the disclosure will now be described, by way of example only, with reference to the drawings, in which:

FIG. 5F is a cross-sectional illustration of an example backing of a transducer, where the segmented surface of the backing is defined by a cloning and shifting operation performed on the segmented surface shown in FIG. 5D.

FIG. 5G is a cross-sectional illustration of an example backing of a transducer, where the segmented surface of the backing is functionally equivalent to the backing show in FIG. 5D.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

Embodiments of the present disclosure provide ultrasonic transducers having a backing that is configured to reduce the impact of reflections generated within the backing on transducer performance. Generally, ultrasonic transducers are formed as multilayer devices, as illustrated in the example transducer 100 shown in FIG. 1. The active layer 110 within the stack of layers that constitutes the transducer may be based, for example, on piezoelectric materials or on capacitive micromachined technology.

For piezoelectric transducers generating longitudinal waves propagating in the normal direction relative to active layer 110, the thickness of active piezoelectric layer 110 plays a primary role in determining the central acoustic resonant frequency of the device. The top and bottom surfaces of the active layer are typically each coated with one or more conductive electrodes (112 and 114) to allow for electrical connection of the transducer to an electrical excitation and/or detection system. Alternatively, a matching layer or backing layer or both may be conductive (e.g. conductive epoxy) and obviate the need for a separate conductive layer.

Figure 2:
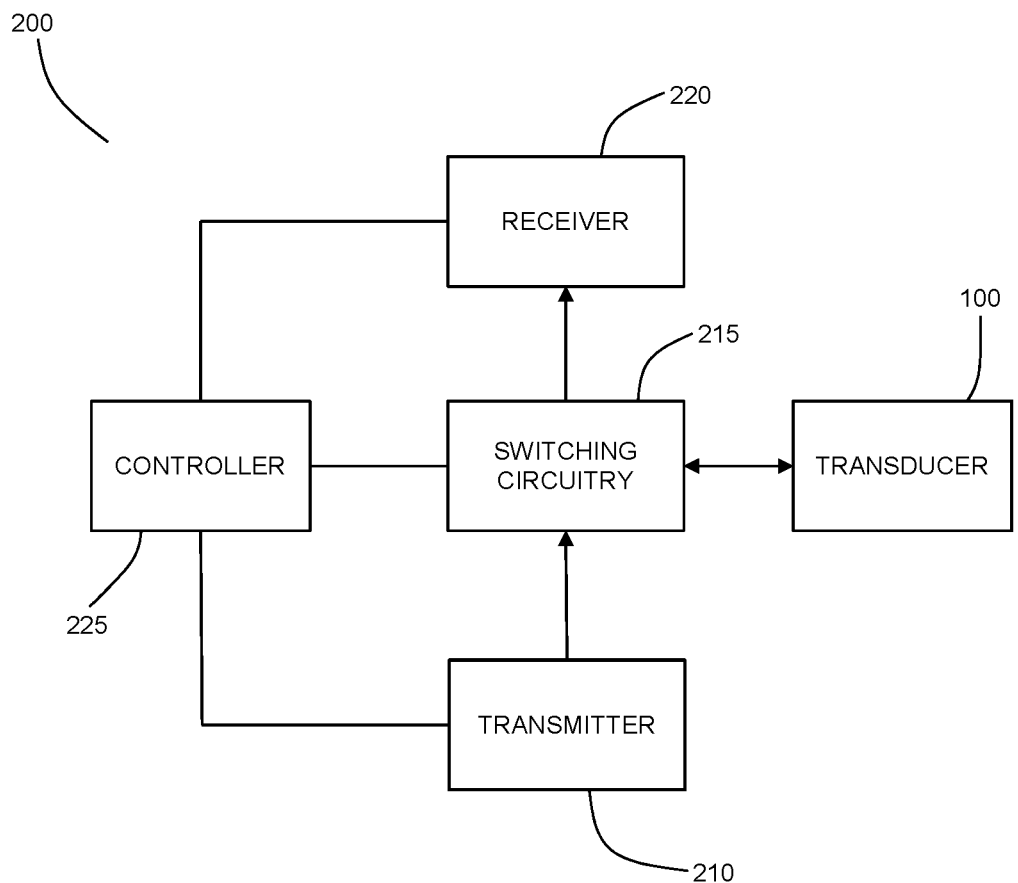
FIG. 2 is an example system for transmitting signals to an ultrasonic transducer and receiving signals from an ultrasonic transducer.

An example of such a system is shown in FIG. 2, and may include a transmitter 210 (e.g. an ultrasonic pulser) that is used generate an electrical waveform for transmitting an ultrasound pulse via ultrasonic transducer 100, and may also be connected to a receiver 220 to sense the acoustic echoes from the imaging medium. Switching circuitry 215 is used to alternate between transmit and receive modes respectively, and a controller 225 (such as a computing device, analog circuitry, digitizer and/or computer hardware) is employed to control switching circuitry 215, and to optionally prepare waveforms transmitted by transmitter 210 and process waveforms received via receiver 220.

Figure 1:
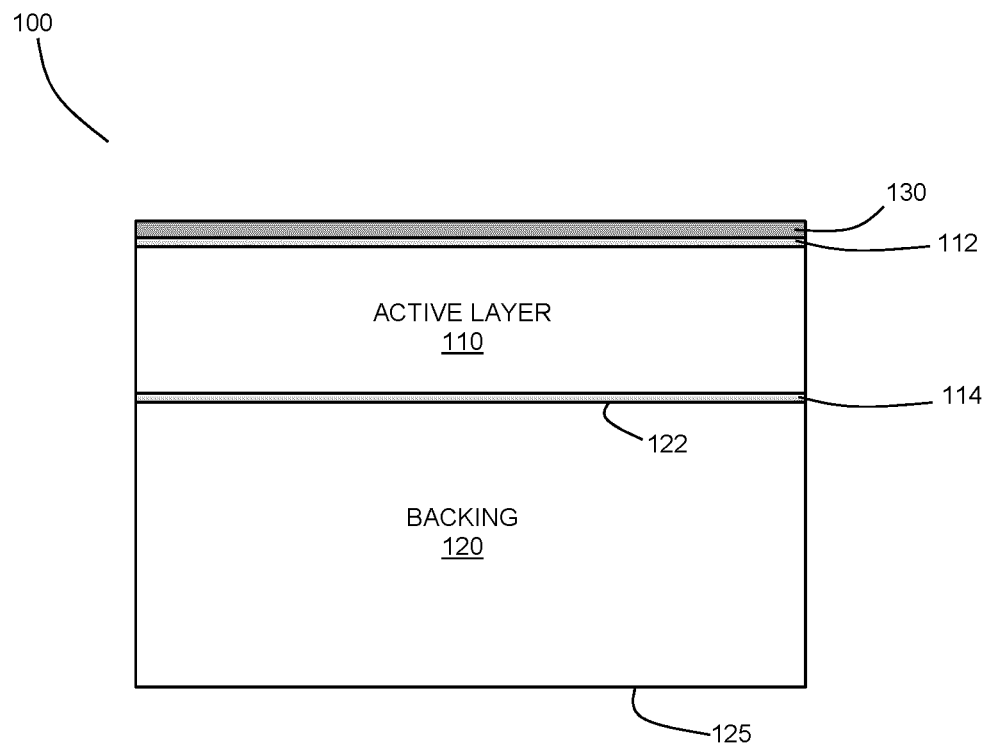
FIG. 1 is a cross-sectional view of an example transducer with a backing having a flat distal surface.

Referring now to FIGS. 1 and 2, in transmit mode, the electric output of transmitter 210 appears across the electrodes of transducer 100, acoustic energy is generated within the active piezoelectric layer 110, and this acoustic energy propagates towards the top and bottom surfaces of the layer. Optionally, one or more matching layers 130 are acoustically coupled to the top surface of the active layer to provide a means to improve the coupling of the acoustic energy into the imaging medium in a temporally efficient manner with minimal acoustic reverberations. The one or more matching layers 130 may be electrically conductive.

In receive mode, a common design involves the use of a receive amplifier and ADC circuitry (shown as receiver 220 in FIG. 2) that are electrically coupled to the electrodes of the transducer. The potential difference within active piezoelectric layer 110 is monitored as a function of time as incident pressure waves to the transducer pass through the active layer. Matching layers 130 provide a means to couple the acoustic energy from the imaging medium and limit the acoustic reverberations within the device.

A transducer with a short time response is desired in ultrasound imaging to maximize the axial resolution of the generated image. The existence of reverberations within the transducer can effectively lengthen the pulse response of the primary transmitted (thus reducing axial resolution of resulting images) or can result in secondary (ghost) pulses that result in undesired artifacts in resulting images, or can cause both effects. Matching layers 130 are provided in order to decrease or substantially eliminate reverberations originating from reflections at the upper interface associated with active layer 110. Matching layers 130 are formed from one or more specific materials with specific acoustic impedances and specific thicknesses. The thickness of each matching layer is usually approximately equal to a quarter wavelength of the central frequency of the device, and is thus related to the speed of sound of the material. Matching layers 130 thus improve the coupling of the acoustic energy from the active layer to the propagating medium (and vice versa) within a bandwidth of frequencies around the center frequency of the device.

Backing 120 is also selected to provide acoustic matching with active layer 110, in other words, to present a specific acoustic impedance to the bottom face of the active layer relative to the acoustic impedance of the active layer itself. The material for backing 120 is also chosen to have a desirable level of acoustic attenuation in order to absorb or otherwise attenuate spurious backwards propagating acoustic energy that enters into the layer. With the use of heavier acoustic impedance backing materials, this layer can help lower the quality factor (or 0) of the resonance of the acoustic layer. Backing 120 may optionally be electrically conductive. A conductive backing may obviate the need for a separate electrode layer 114.

Acoustic energy that propagates through active layer 110 and towards the bottom surface of the active layer will be partially reflected and partially transmitted at the interface between the bottom surface of the active layer and the top surface of the backing layer. The electrode thickness is often sufficiently thin (e.g. typically less than one micron) that it does not play a significant role in the acoustic response of the device. The extent of the reflection is a function of the difference in the acoustic impedance of the two layers. The reflected energy will propagate towards the matching layers 130 and into the imaging medium. The transmitted energy, ideally, is completely attenuated within backing 120 and would not contribute to the transmitted acoustic pulse. Theoretically, such a result could be achieved by an infinitely thick backing layer of minimal attenuation. More practically, this can be approximately achieved by a backing material of a specific attenuation that is thick enough such that the reflected signals off of the bottom surface of the backing layer are substantially reduced to a level below any perceived noise floor of the system.

In cases where the transducer must fit within a limited volume of space, such as a transducer capable of side-viewing in an imaging catheter or other minimally invasive imaging probe, the reflected signals off of the bottom surface 125 of the backing layer may result in a secondary pulse that trails the initial imaging pulse. The time interval between pulses would be approximately equal to the time required for an acoustic signal to travel a distance equal to twice the thickness of the backing of the transducer. In other words a primary signal passing into the backing material will travel the thickness of the backing material, reflect off the bottom surface 125 of backing 120 and then travel the thickness of the backing material again before partially re-entering the active layer 110 of the transducer stack. The intensity of the signal will be lower than the initial pulse due to splitting of the energy at both the top surface 122 and the bottom surface 125 of backing 120, as well as the attenuation loss through the backing layer but may still be appreciable when visualized in an ultrasound image, especially where detected signals are often log-compressed to increase the dynamic range of sensed signals.

Typically, as the thickness of the backing 120 is reduced, the time interval between the primary imaging/receiving pulse and secondary reverberation pulses is shortened and the intensity of the secondary pulse increases relative to the primary pulse. For transducers where size constraints prohibit a thick enough backing (for a given backing material) to adequately attenuate the secondary pulse, a secondary pulse that may result in imaging artifacts may appear to be inevitable.

Figure 3:
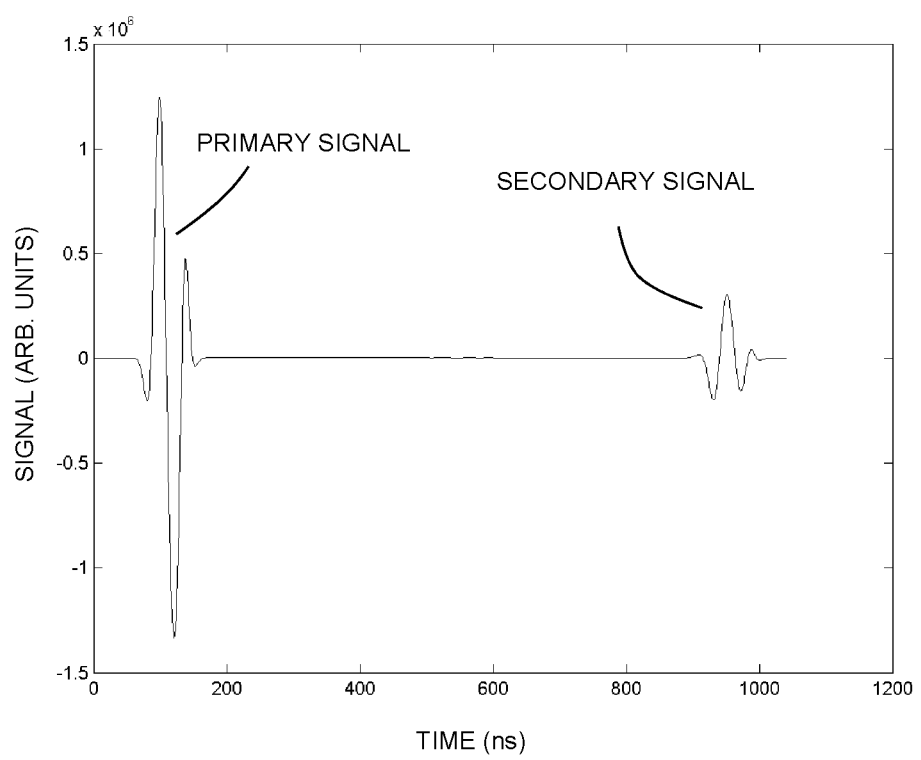
FIG. 3 is a plot showing the secondary signal produced by the reflection of acoustic waves from the distal surface of a transducer.

An example of a secondary pulse, obtained in receive mode, for a transducer with an insufficiently thick or insufficiently attenuative backing or both, is shown in FIG. 3. As can be seen, the primary signal 310 that is detected is followed by a secondary signal that is an attenuated version of the primary signal. In imaging applications in which the imaging region includes acoustic scattering that are spread over an axial region that is greater or equal to the round trip path through the backing, the presence of the secondary signal can be difficult to extract from the primary signal portion, leading to an image of reduced signal to noise.

Selected embodiments are henceforth described in which a transducer is provided with a backing having a proximate surface that is proximate to the active layer and a further surface located below the proximate surface, where at least a portion of a further surface of the backing is spatially segmented to reduce the amplitude of secondary signals produced by acoustic waves reflected therefrom. As described below, in some embodiments, spatial variations may be provided in the thickness of the backing such that the backing has a spatially variable thickness, thereby breaking up the spatial coherence of the reverberations within the backing by introducing a spatial variation in the time of flight of reverberations within the backing. The break-up of the spatial coherence of the wavefronts of the reverberations is beyond the effects created by scatterers alone. In some embodiments, the backing may include a segmented surface that is configured such that interference occurs among the reflected acoustic wavefronts, thereby reducing the susceptibility of the transducer to reverberations.

As further described below, the transducers with a segmented backing surface may be employed as ultrasonic imaging elements and devices. Ultrasound imaging is based on measuring the amplitude of incident acoustic waves (or wavefronts) onto the active layer of the transducer stack and by keeping track of the arrival time of the signals to distinguish the distance of the originating signal or reflection within the imaging medium. Huygens' principle states that every point on a wavefront may be considered a source of secondary spherical wavelets which spread out in the forwardly propagating direction at the speed of propagation within the medium. The new wavefront is the tangential surface to all of these secondary wavelets. The electrodes (e.g. a conductive layer), across the full aperture of the active acoustic layer, integrate the amplitudes of all incident waveforms at any given time.

In receive mode, the incident waves that are principally normally incident onto the transducer are recorded as the primary signal and if any of the waves that propagate into the backing follow a path that leads part of the energy back into the active layer of the transducer, then these signals are recorded as secondary signals. If the path of the waves within the backing is divided into different segments such that the distributed Huygens's wavelets are spatially decorrelated, then the wavefront will be broken up and different portions of the energy will return to the active layer at different moments in time and the instantaneously summed amplitude of any reverberation across the entire aperture of the acoustically active layer is small.

As noted above, decorrelation may be achieved by varying the thickness of the backing material, such that a further surface of the backing includes a plurality of segments. By weighting the percentage of the backing at each variable thickness, the amplitude and the relative phase of each segment of the reverberation returning to the active layer of the transducer stack can be controlled.

Figure 4A:
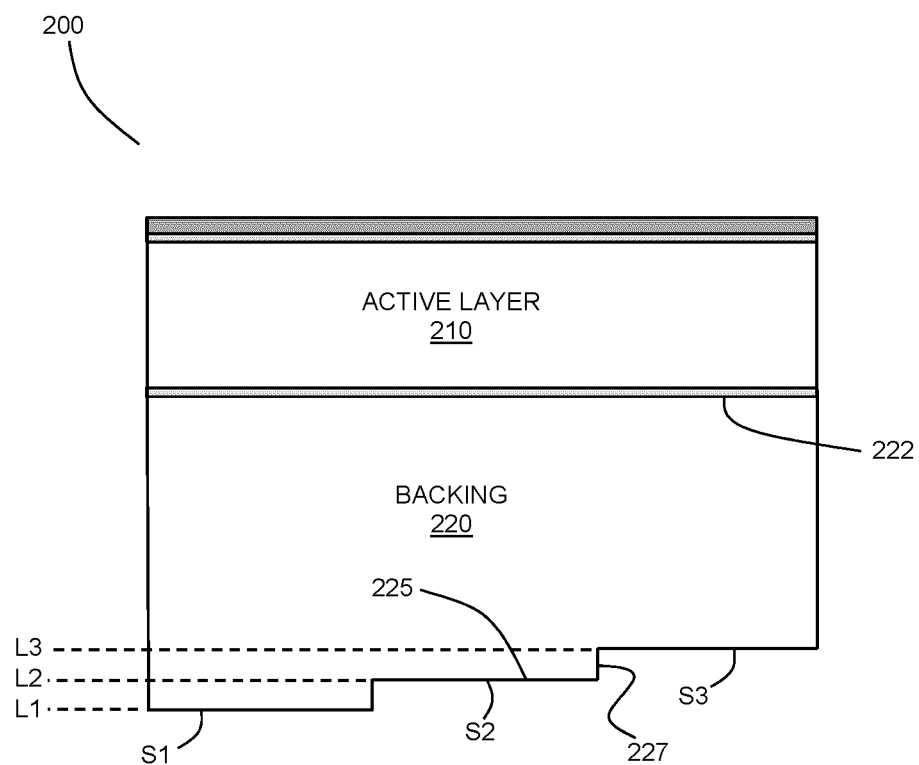
FIG. 4A is a cross-sectional illustration of an example transducer having a backing with a segmented surface.

FIG. 4A illustrates a non-limiting example implementation of such an ultrasonic transducer, shown as a cross-sectional view. The backing 220 of transducer 200 has a proximate surface 222 proximate to the active layer of the transducer, and a segmented surface 225 below the proximate surface that is configured to reduce the effect of acoustic waves reflected therefrom. The segmented surface includes surface segments S1-S3 that are approximately parallel to planar surface 222, such that the surface segments S1-S3 reflect acoustic waves back towards active layer 210. As shown in the Figure, three of the surface segments S1-S3 are spatially offset in a longitudinal direction (a direction that is approximately perpendicular to planar surface 222, such that the surface segments reside at three spatially offset levels L1-L3. The present FIG. 4A shows the non-limiting example case of three levels, where, in this non-limiting example embodiment, the portion of the backing that is segmented is the full extent of the backing.

Figure 4B:
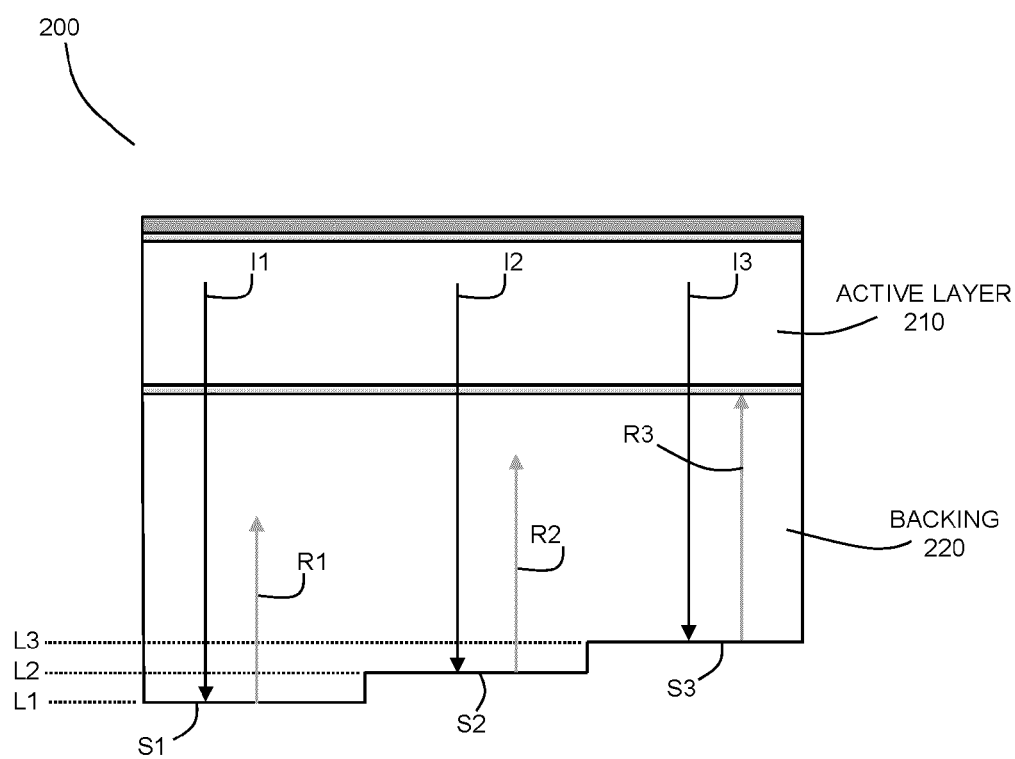
FIG. 4B shows the reflection of acoustic waves from the segments of the segmented surface shown in FIG. 4A.

As shown in FIG. 4B, the spatial offsetting of the segments S1-S3 to three or more levels (L1-L3) results in a decreased amplitude of secondary signals produced within active layer 210 by the reflected acoustic waves when the transducer is used in receive mode. In some embodiments, this reduction in the amplitude of secondary signals occurs at least in part due to the temporal stretching and/or spreading of the reflected acoustic waves. The temporal stretching and/or spreading occurs because the multiple reflections from the segments at the three or more levels results in retarded components of the reflected waves that produce the secondary signal. This is apparent in FIG. 4B, where the three reflected waves R1-R3, resulting from reflections of incident waves I1-I3, reflect towards active layer 210 with different time delays, spreading their power over a broader time duration, thereby reducing the amplitude of a secondary signal generated in active layer 210. Accordingly, each level has associated therewith a different backing thickness.

In some embodiments, the spatially offsetting of the levels, and the areas of the segments at the different levels, is provided to produce destructive interference in the generation of a secondary signal from the reflected acoustic waves originating from neighbouring levels, thereby resulting in a reduction of the secondary signal produced via the active layer.

When the transducer is used to transmit an acoustic signal, the wavefronts reflecting from the different segmented levels will destructively interfere as the wavefronts diffract. When the transducer is used to receive an acoustical signal, the destructive interference occurs in the electrical excitation induced in the active layer by the various reflected acoustic waves, as opposed to destructive interference directly amongst the reflected acoustic waves.

The above mentioned destructive interference effects may be achieved by controlling the spacing between adjacent levels, such that the longitudinal spatial offset $\Delta L_{i,i+1}$ between neighbouring levels i and i+1 satisfies $\Delta L_{i,i+1} \sim m_{i,i+1} \lambda/4$, where $m_{i,i+1}$ is an odd whole number, and where $\lambda$ is an operational wavelength of the transducer. It will be understand that the value of $m_{i,i+1}$ may vary among different pairs of neighbouring levels. The spatial waveform of the signal pulse should have a pulse length exceeding twice the level spacing, such that destructive interference produced by reflected acoustic waves from adjacent segments may occur. It will be understood that the spacing between levels can be adjusted to account for the broadband nature, of the transducer and therefore the path difference can deviate from the approximately odd multiple of quarter wavelength by an amount that results in the path length being equivalent to a quarter wavelength of any of the frequencies within a selected portion of the bandwidth of the transducer response. Such an embodiment is described further below.

Figure 4C:
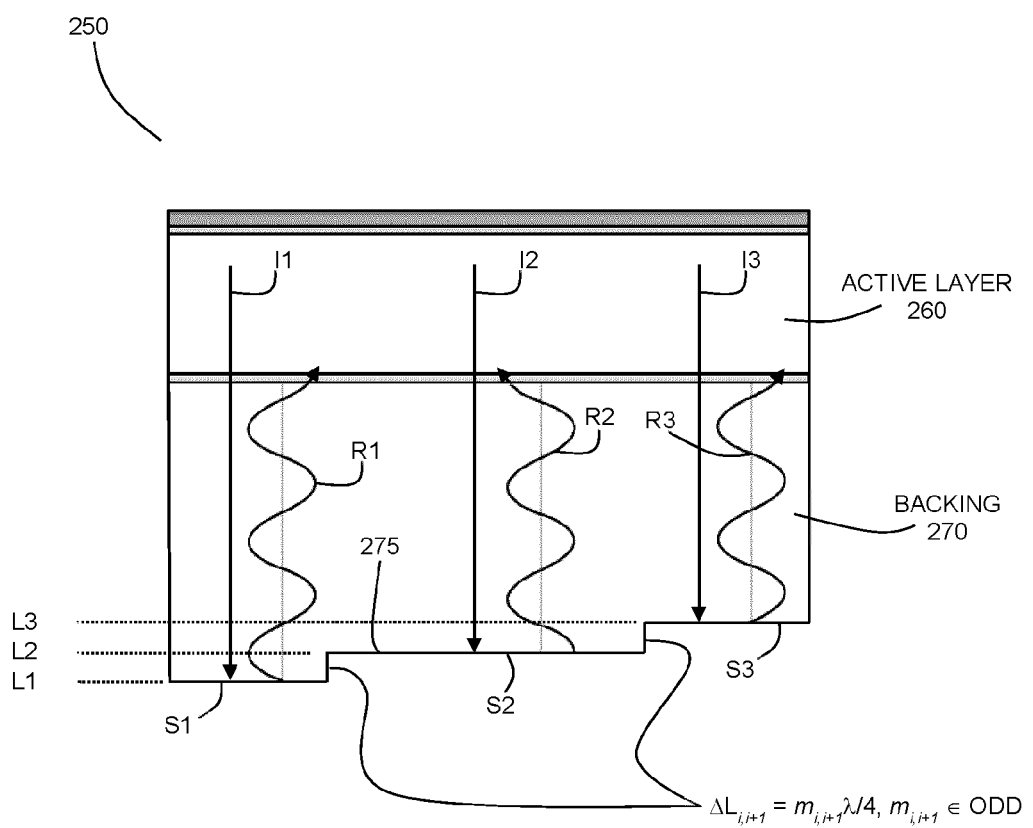
FIG. 4C is a cross-sectional illustration of an example transducer having a backing with a segmented surface defined by three levels, where the step between adjacent levels is approximately equal to an odd number multiple of an operational wavelength associated with the transducer.

Such an example embodiment is illustrated in FIG. 4C, where example transducer 250 includes backing 270 having segmented surface 275, where three segments S1, S2 and S3 are laterally offset by an odd multiple of a quarter wavelength of the propagating waveform within the backing layer. The specific embodiment shown in the Figure illustrates the example case where the longitudinal spatial offset $\Delta L \sim \lambda/4$ (note that this Figure is not to scale). As shown in the Figure, R1 and R2 differ from each other by a phase delay of $\pi$. Similarly, R2 and R3 differ from each other by a phase delay of $\pi$. This phase delay results in destructive interference in the generation of a secondary signal, in the electrical domain, by the reflected waves as they propagate through active layer 260. It is therefore apparent that the embodiment shown in FIG. 4C reduces the impact of the reflected waves on artifacts generated by their passage through active layer 260, both due to the temporal spreading of the reflected acoustic waves, and due to the interference of the reflected waves.

The time interval between the primary pulse and the arrival of the secondary reverberation of the reflected signal from each level will be dependent on the path length associated with the backing thickness associated with the level. The level with the minimum path length is the level with the minimum thickness and this level will correspond the shortest time interval. Similarly, the level with the maximum path length is the level with the maximum thickness and this level will correspond to the longest time interval. For a short primary pulse, the pulse duration of the secondary reverberation pulse will be approximately the time difference between the shortest and longest time intervals.

As noted above, one specific example implementation involves levels with a lateral offset of approximately $\lambda/4$. This embodiment may be useful or beneficial when attempting to suppress reverberations from short pulses, because this minimal step among levels ensures that the reflected waves from adjacent levels have a minimal relative shift in time in order to achieve efficient destructive interference. In other words, if the relative time delay between adjacent reflected acoustic waves is large (e.g. on the order of the pulsewidth, as opposed to on the order of the period of the fundamental frequency of the pulse), then the amplitudes of the adjacent reflected acoustic waves may be very dissimilar and thereby prevent achieving sufficient destructive interference, especially for the leading and trailing edges of the pulse where the pulse envelope varies strongly with time.

Although the configuration shown in FIG. 4C illustrates an example embodiment in which there is one segment per level (S1:L1, S2:L2, and S3:L3), it is to be understood that this is but one example configuration, and that in other embodiments, a given level may have two or more segments associated therewith. In such a case, the two or more segments associated with a given level are approximately co-planar, such that they have a common backing thickness associated therewith. An example of such an alternative configuration is shown in FIG. 4D, which illustrates an embodiment that is functionally equivalent to that of FIG. 4C, since the segmented surface 325 is provided such that the total area of associated with each level, which is obtained by summing the area of the segments making up each level, is equal for the two embodiments.

Figure 4D:
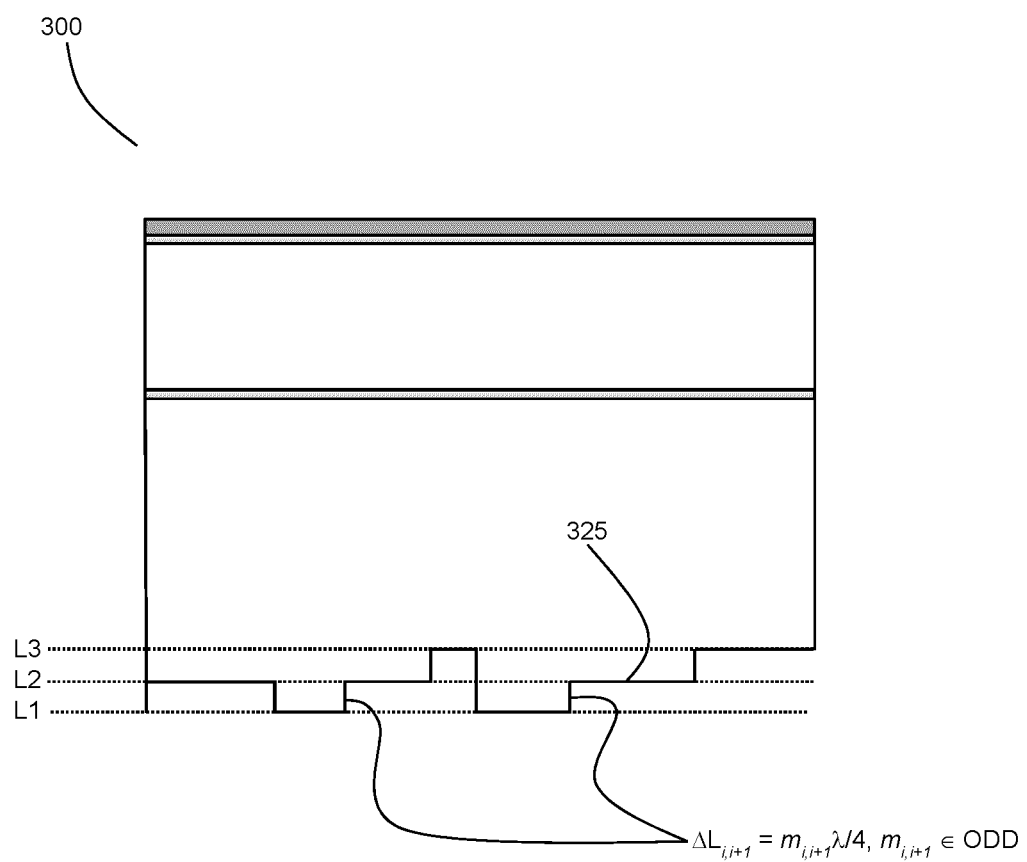
FIG. 4D shows an example transducer having a backing with a segmented surface that is functionally equivalent to the transducer shown in FIG. 4C.

Therefore, even though the two embodiments shown in FIGS. 4C and 4D employ different segmented surface geometries, they are expected to exhibit similar performance in suppressing artifacts associated with spurious reverberations within the transducer backing. It is noted, however, that in some embodiments and applications, it may be beneficial to provide levels with one segment per level, for example, in order to simplify the cost and complexity of fabrication, and/or to avoid or reduce the number of intermediate longitudinal side walls that may degrade the performance of a device due to scattering effects.

Comparing FIGS. 4C and 4B, it can be seen that the areas of the segments forming the different levels, while being approximately equal in FIG. 4B, are unequal in FIG. 4C. In FIG. 4B, the levels were spatially offset in order to spread the reflected acoustic wave over a broader time duration, so as to produce a secondary signal with a reduced amplitude in receive mode. In FIG. 4C (and FIG. 4D), however, adjacent levels are also spatially offset by odd multiples of a quarter of the operational wavelength of the transducer, such that the reflected acoustic waves from adjacent surfaces are out of phase when they propagate through the active layer.

The reflected acoustic waves from the various segments together produce a net response within the active layer, based on their combined effect. The intensity of the reflected signal from each level will be proportional to the fractional area of the level relative to the overall area of the backing. In one embodiment, in order to produce destructive interference at a given moment in time during the propagation of the reflected acoustic waves through the active layer, the contributions from the reflected acoustic waves associated with the odd numbered levels (e.g. levels 1, 3, 5, . . . ) and the reflected acoustic waves associated with the even numbered levels (e.g. levels 2, 4, 6, . . . ) should be approximately equal. This condition can be met, for example, when the total area of the odd levels is approximately equal to the total area of the even levels.

It will be understood that the embodiment shown in the FIGS. 4A-4D, which shows a transducer including three levels, is merely provided as an illustrative example, and that the number of levels may vary in other example implementations. For example in some embodiments, the number of spatially offset levels may be two. Such an embodiment may be useful, for example, in applications in which a small backing size is sought to support the inclusion of the transducer within a minimally invasive catheter, such as an ultrasonic imaging and/or therapeutic catheter (or a multi-modality catheter including ultrasound for one or more imaging and/or therapeutic modalities). Moreover, it may be beneficial to employ such a low-profile segmented backing in applications involving narrowband acoustic signals, or, for example, in applications involving Doppler ultrasound. In other embodiments, the number of spatially offset levels may be three or more. As noted above, and further described below, in some embodiments, the dimensions of the transducer are sufficiently small for use within a minimally invasive catheter (example dimensions of such catheters are described below).

In some embodiments, the surface areas of the levels may be provided to compensate for depth-dependent attenuation in order to achieve suitable interference of reflected acoustic waves. Such depth-dependent attenuation occurs due to the increased propagation path length within the backing that is experienced by acoustic waves that are reflected by segments having larger local backing thicknesses. For example, if two levels are separated by a quarter of a wavelength, then the acoustic wave reflected from the deeper segment (having a larger local backing thickness) will experience a reduction in the acoustic intensity by $e^{-\alpha\lambda/2}$, where $\alpha$ is the power attenuation coefficient of the backing, relative to the acoustic beam reflected by the shallower segment (having a smaller local thickness). In order to compensate for the intensity loss of the wave reflected from the deeper segment, the surface area of the deeper segment can be increased by a factor of approximately $e^{\alpha\lambda/2}$ (or equivalently, the surface area of the shallower segment can be reduced by $e^{-\alpha\lambda/2}$). This compensation ensures that the intensity of the two reflected and phase-shifted acoustic waves are approximately equal, such that the two waves interfere effectively in the active layer.

Referring now to FIG. 4C, it can be seen that the first and third levels, L1 and L3, respectively, have approximately equal areas, and that the second level L2 (the middle, or intermediate level) has an area that is approximately double that of the first or third levels, such that the area of the second level (the only even level) is approximately equal to the combined area of the odd levels (the sum of the area of the first and third levels). As can be seen in FIG. 4C, the acoustic waves reflected from levels L1 and L3 are related by a phase delay of $2\pi$, such they add constructively, while the acoustic wave reflected from level L2 is out of phase with the acoustic waves reflected from levels L1 and L3. Accordingly, the net effect of the various reflected acoustic waves sum within active layer 260 such that their contributions to the generation of the secondary signal destructively interfere.

It is noted, however, that in some embodiments that involve a backing configured to employ interference of reflected acoustic waves, the areas of the segments forming the different levels may be equal, while still achieving interference. For example, in embodiments in which the number of levels is an even number, the levels may have approximately equal areas, as this would produce reflected acoustic waves from the even and odd levels with substantially equal contributions, thereby resulting in destructive interference and suppression of the secondary signal.

Accordingly, in light of the aforementioned discussion of the role of the areas of the segments, it will be understood that in some embodiments, the number of different segments that are included at a given level (or are associated with a given backing thickness), and the areas of the segments included at a given level, may be chosen, designed or selected such that the weighting of the areas of the segments produces suitable interference of the reflected acoustic waves from the various levels.

Figure 4E:
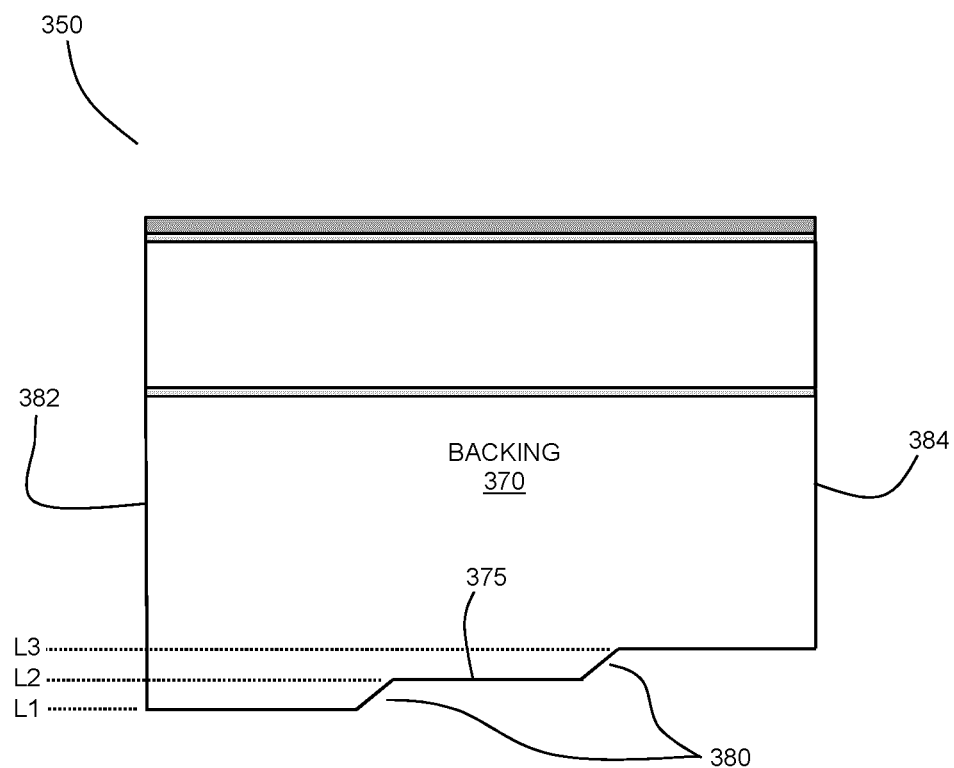
FIG. 4E is a cross-sectional illustration of an example transducer having a backing with a segmented surface defined by three levels, where the transition walls between the levels are sloped.

The preceding embodiments show example implementations in which the different levels of the segmented surface are separated by steep transition walls that are approximately perpendicular to the planes of the segments (such as transition wall 227 in FIG. 4A). The effects of such vertical walls will depend on the diffusion/deflection that occurs at the vertical walls for each given reflection from a segmented surface and what the resultant phase relationship will be for each portion of the reflection that returns to the active layer. It will be understood, however, that in other embodiments, one or more of the transition walls may be sloped. An example implementation with a sloped transition wall is illustrated in FIG. 4E, where transducer 350 has a backing surface 375 that includes sloped transition walls 380. The sloped side walls may take on a wide variety of geometries, such as straight slopes as shown in FIG. 4E, or, for example, curved slopes. The geometry of the slope may, in some cases, be dictated by the manufacturing process, and its inherent tolerances. In some embodiments, sloped transition walls may be provided that are angled, for example, as shown in FIG. 4E, to provide anechoic surfaces that reflect a portion of an incident acoustic beam in a lateral direction, thereby increasing the path length of the reflected acoustic wave, and its associated attenuation. In some embodiments, the side walls 382 and 384 of the backing 370 may include additional anechoic surfaces or features.

Although the preceding embodiments illustrate examples in which the segmented surface is a distal surface of the backing, it will be understood that the segmented surface may be provided or formed in any surface of the backing that is further from the surface proximate to the active layer. For example, in some embodiments, the segmented surface may be formed in a further surface that is an internal surface within the backing. Such an internal surface separates two different backing layers having different acoustic impedances, such that acoustic reflections are generated by the internal surface.

Figure 4F:
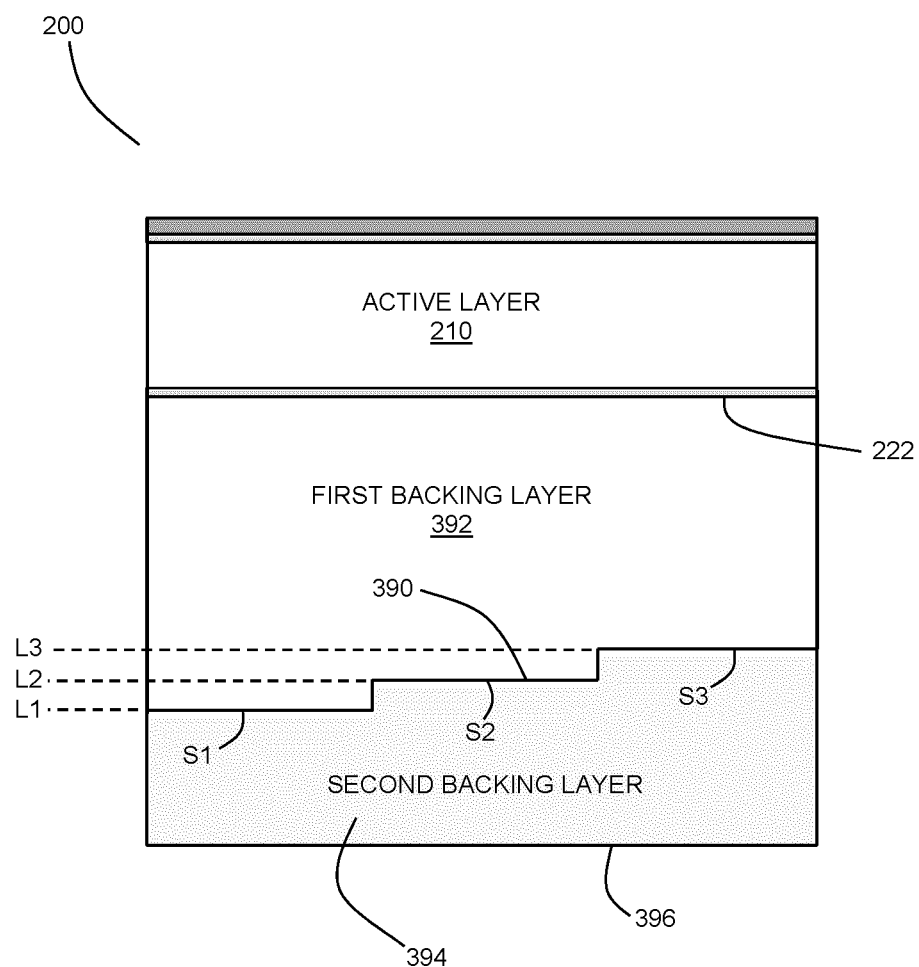
FIG. 4F is a cross-sectional illustration of an example transducer having a backing with an internal segmented surface formed between two layers with unequal acoustic impedances.

FIG. 4F illustrates an additional example implementation of such an embodiment, in which the segmented surface is formed in an internal surface 390 formed between first backing layer 392 and second backing layer 394. Backing layers 392 and 394 have different acoustic impedances, such that an acoustic reflection is generated by internal surface 390. The presence of second backing layer 394, having a non-segmented distal surface 396, may be beneficial in reducing or preventing the accumulation of bubbles that may otherwise form at a segmented distal surface.

The acoustic impedances of the layers may be selected such that the acoustic impedance of second layer 394 is lower than that of first layer 392, such that the acoustic impedance mismatch between second layer 394 and the region external to the backing is reduced, such that reflections from surface 396 are reduced. Surface 396 may also have a sloped or anechoic surface geometry in order to reduce the generation of acoustic reflections that propagate back towards the active layer. Second layer 394 may be formed from an attenuating backing material having a thickness that is sufficient for substantially reducing the amplitude of reflections from surface 396 that propagate back through internal surface 390 (e.g. reducing the amplitude of reflections by 50% or more, 75% or more, 90% or more, or 95% or more).

In some embodiments, the backing may be segmented such that the minimum thickness segment of the backing is sufficiently thin that the reverberation pulse interferes with the primary pulse.

Various embodiments described herein refer to an "operational wavelength" of a transducer. The term "operational wavelength" may be defined as described below. When designing a piezoelectric based ultrasound transducer stack, the thickness of the active layer is often substantially smaller than the width of the active layer (typically $\frac{1}{10}^{th}$ the size or smaller). This is done to separate the frequency of the fundamental thickness resonant mode of the layer from any lateral resonance mode. Within any propagating material or medium (such as conductive silver epoxy or human tissue) the propagating waveform will have a fundamental wavelength that is related to the frequency of the fundamental resonance mode through the speed of sound of the material or medium, according to the relation: Wavelength=speed of sound/frequency. In some embodiments, the operational wavelength may be this fundamental design wavelength.

In real transducers, materials are not perfect (ideal) resonators and therefore the fundamental frequency is actually a band of excited frequencies that can be characterized by a center frequency and a bandwidth of excited frequencies. Matching layers and backing layers are added to effectively couple as much of the resonant energy out the front face of the transducer stack and into the propagating medium in as short a time as possible. This will result in yet a broader frequency response of the stack, (i.e. broader bandwidth of excited frequencies) allowing for the transducer stack to more closely replicate an ultrasound pulse response waveform from a short excitation transmit signal (say a single cycle waveform) as well as from a more narrow band excitation pulse such as a tone burst of several cycles in duration. Fabrication tolerances can also result in deviations of the time and frequency response of the transducer. In some embodiments, the operational wavelength associated with the transducer may be the wavelength within the frequency response of the stack, such as the center wavelength. For example, in some embodiments, the operational wavelength associated with the transducer may include any wavelength within this combined design, excitation pulse, and fabrication tolerance dependent bandwidth.

It is further noted that the residual secondary signals produced by the reflection from the segmented surface may have an envelope such that they have a different frequency spectrum than the primary signal. Accordingly, in some embodiments, any step between levels need not be exactly an odd multiple of a quarter of an operational wavelength. In some embodiments, a given operational wavelength corresponds to any frequency within a given percentage of the waveform bandwidth (such as 50% of the bandwidth), relative to the center frequency of the waveform. For example: for a short pulse excitation waveform with a center frequency of 10 MHz and a bandwidth of 10 MHz, one may consider selecting the value of the step to be an odd multiple quarter wavelength based on frequencies within the range of approximately 7.5 to 12.5 MHz. In other embodiments, the selection of the height of a step may be chosen in relation to an operational wavelength that is selected on frequencies within other ranges, such as, for example, frequencies within 10%, 20%, 30% or 40% of bandwidth, relative to the center frequency.

The backing may be formed from a wide variety of materials, including, but not limited to, epoxy, powder loaded epoxy, porous metals, porous ceramics, and engineered 2-phased composite structures. In embodiments in which the phase of the reflected acoustic waves from different segments is employed to produce destructive interference, the backing may be formed from a material that otherwise would have been expected to substantially preserve the coherence of acoustic waves propagating therein. Examples of such backing materials include single phase materials (epoxies, polymers, metals), powder loaded epoxies whereby the size of the doping particulates are not well tuned to the scattering of ultrasound at the operational wavelength. As noted above, the backing thickness may be such that the backing may not sufficiently attenuate the acoustic energy by means of acoustic absorption and scattering alone. The backing may be coated with a layer that is hydrophilic and/or electrically insulating. Non-limiting examples of suitable coatings include Parylene and $TiO_2$.

Although the above embodiments disclose example transducers with a backing having a surface that is segmented such that the segments vary along one dimension, it will be understood that the backing may be segmented in such that the segments vary in two spatial dimensions. In other words, the segmented surface of the backing may vary in up to three dimensions—one dimension defining the different levels, and one or two dimensions defining the variations in the segments.

In one example implementation, at least a portion of a further surface of the backing may be segmented into a plurality of square and/or rectangular segments, such that the segments vary in two dimensions. In another example implementation, at least a portion of a further surface of the backing may be segmented into a series of annular segments surrounding a central circular or elliptical segment.

It is to be understood that the phrase "segmented surface", as used herein, refers to a further surface of a transducer backing where at least a portion of the further surface is segmented into segments that define three or more levels, as described above. In some embodiments, only a portion of the further surface is segmented. For example, in one example implementation, the further surface of the backing may have one or more functional devices attached thereto over a first portion thereof, and the remaining portion of the further surface may be segmented as described above. One example of a functional device attached to a portion of the surface of a transducer backing is an angle detection transducer, as described in Patent Cooperation Treaty Patent Application No. PCT/CA/2012/050057, titled "ULTRASONIC PROBE WITH ULTRASONIC TRANSDUCERS ADDRESSABLE ON COMMON ELECTRICAL CHANNEL" and filed on Jan. 31, 2012, which is incorporated herein by reference in its entirety.

In some embodiments, the segmented surface is configured to suppress secondary signals generated by the reflection of short pulses, such as pulses having an envelope with a time duration approximately equal to approximately 1 cycle, two cycles, or three cycles. For example, a typical medical imaging pulse is a short pulse in time that may last for 1-2 cycles (1-2 wavelengths) or more. The envelope of a short time pulse waveform can be considered to have a rising, or positive, slope and followed, shortly thereafter, by a falling, or negative, slope. This is in contrast to a tone burst of several wavelengths where the envelope of such a pulse waveform would be characterized by an initial rising slope with a segment of a substantially flat envelope of zero slope followed by a final falling slope.

In one embodiment, in order to suppress the effect of the rising and falling edges of a reflected signal, the segmented surface may be formed as a plurality of 'n' stepped segments, whereby each adjacent segment creates an approximately additional ½ of an operational wavelength delay in the signal such that the leading and trailing edge of the signal is reduced to 1/n in strength and the contributions from all intermediate reflected signals cancel destructively. Such an embodiment is illustrated in Example 1 below.

In one embodiment, the segmented surface may be defined as follows. A first set of segments is defined by two adjacent segments, longitudinally offset by approximately a quarter of an operational wavelength of the transducer, thereby defining two levels of the segmented surface. An additional portion of the segmented surface is then formed by cloning the first set of segments, and offsetting the cloned set by approximately a quarter of an operational wavelength (with m=1) of the transducer.

Figure 5A:
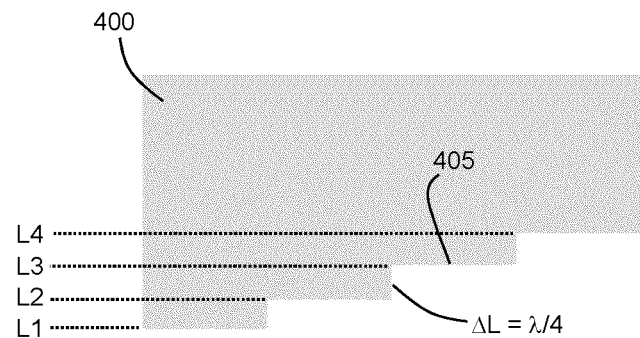
FIG. 5A is a cross-sectional illustration of an example backing of a transducer, where the segmented surface of the backing includes four stepped levels.
Figure 5B:
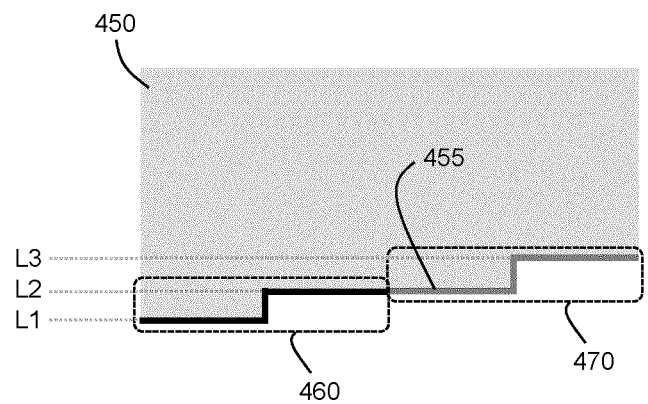
FIG. 5B is a cross-sectional illustration of an example backing of a transducer, where the segmented surface of the backing is defined by a cloning and shifting operation.

An example implementation of this method of defining a segmented surface is shown with reference FIGS. 5A and 5B, which show the backing portion of a transducer. In FIG. 5A, segmented surface 405 of backing 400 is formed from four segments, defining levels L1-L4, where each level has a common surface area, and each level is stepped and shifted from another by a quarter of an operational wavelength of the transducer. In contrast, FIG. 5B shows a backing 450 having a segmented surface 455 that is defined based on the cloning and shifting of first set of segments 460. Specifically, second set of segments 470 is a copy of first set of segments 460 that has been shifted upward by a quarter of an operational wavelength of the transducer.

Figure 5C:
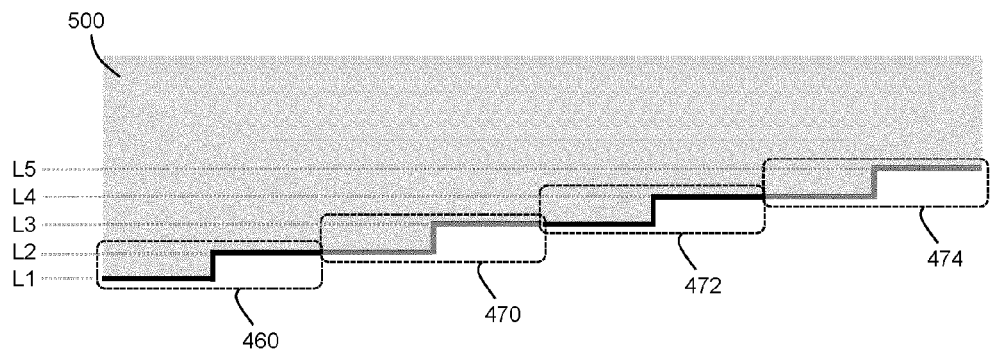
FIG. 5C is a cross-sectional illustration of an example backing of a transducer, where the segmented surface of the backing is defined by multiple cloning and shifting operations.

This method of defining a segmented surface by cloning and offsetting may be repeated more than once. An example embodiment of a segmented surface formed from three cloning and shifting operations is shown in FIG. 5C. Segmented surface 505 of backing 500 is formed by multiple cloning and shifting operations to define second, third and fourth sets of segments 470, 472 and 474 from first set of segments 460.

In another embodiment, a segmented surface can be defined by the following double cloning and shifting method. One or more cloning and shifting operations may be performed to define a first segmented surface portion, which may be referred to as a superset of segments. One or more cloning and shifting operations are then performed using the superset of segments to define a segmented surface including at least one additional superset of segments that is cloned and shifted relative to the first superset of segments.

Figure 5D:
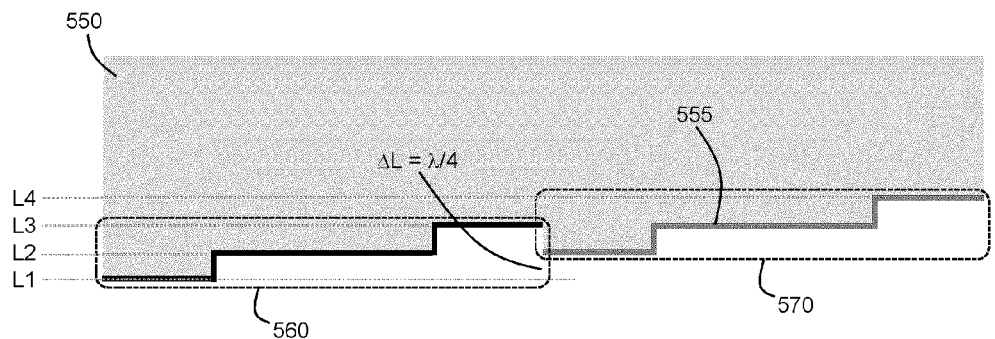
FIG. 5D is a cross-sectional illustration of an example backing of a transducer, where the segmented surface of the backing is defined by a cloning and shifting operation of a superset of segments.

An example implementation of this embodiment is shown in FIG. 5D, in a superset of surfaces is cloned and shifted to produce segmented surface 555 of backing 550. This segmented surface is produced by cloning and shifting first superset 560 to obtain second superset of surfaces 570. As seen in the Figure, superset 570 which is shifted by a quarter of an operational wavelength relative to first superset 560. First superset of surfaces 560 is itself obtained by the cloning and shifting operation shown in FIG. 5B.

Figure 5E:
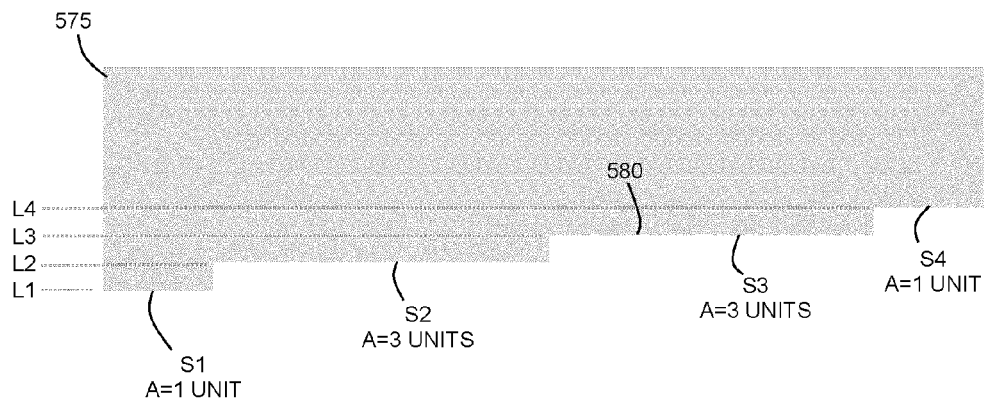
FIG. 5E is a cross-sectional illustration of an example backing of a transducer, where the segmented surface of the backing is functionally equivalent to the backing show in FIG. 5D.

As described above, the spatial distribution of segments associated with a given level (or local backing thickness) can be varied, and one segment can be divided into several segments having an equivalent total area, since the amplitude of the secondary pulse is the sum across the entire area of the electrode. This is illustrated in FIG. 5E, which shows backing 575 having segmented surface 580 for which the areas of the segments at each level are equal to those in FIG. 5D, such that segmented surface 580 is functionally equivalent to segmented surface 555 of FIG. 5D.

Accordingly, it should be understood that spatial permutations of one-dimensional or two-dimensional segments can be categorized by the extent to which the full energy content of the initial wave transmitted into the backing, is cancelled, due to phase interference by the various reflections off of the bottom surface of the backing layer and can be expressed in terms of the reduction of the intensity of any secondary signal and its relation to the intensity of the primary pulse.

It will be understood that the aforementioned method of cloning and shifting a superset may also be performed one or more additional times to define surfaces with additional levels and complexity. For example, backing 600 of FIG. 5F shows a segmented surface 605 that has been defined based on a cloning and shifting operation in which the first superset 610 is taken to be the segmented surface shown in FIG. 5D. Superset 610 is cloned and shifted to obtain additional surface portion 620. The resulting complex segmented surface is functionally equivalent to segmented surface 655 of backing 650 that is shown in FIG. 5G.

Figure 6:
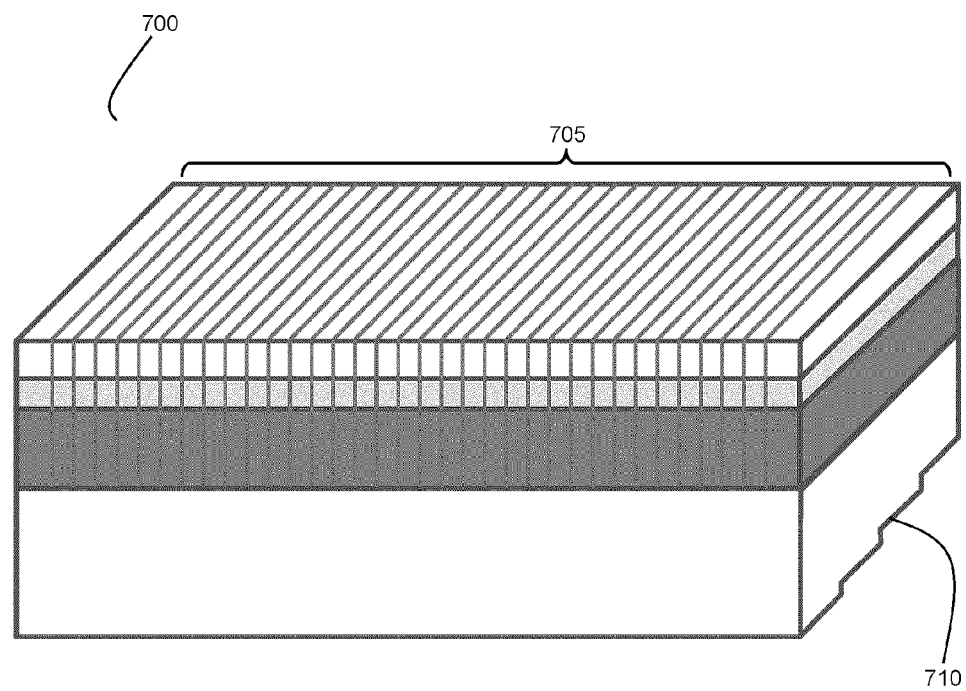
FIG. 6 is an illustration of an example embodiment of an ultrasonic array including an array of ultrasonic transducers in which a further surface of the backing is segmented.
Figure 7A:
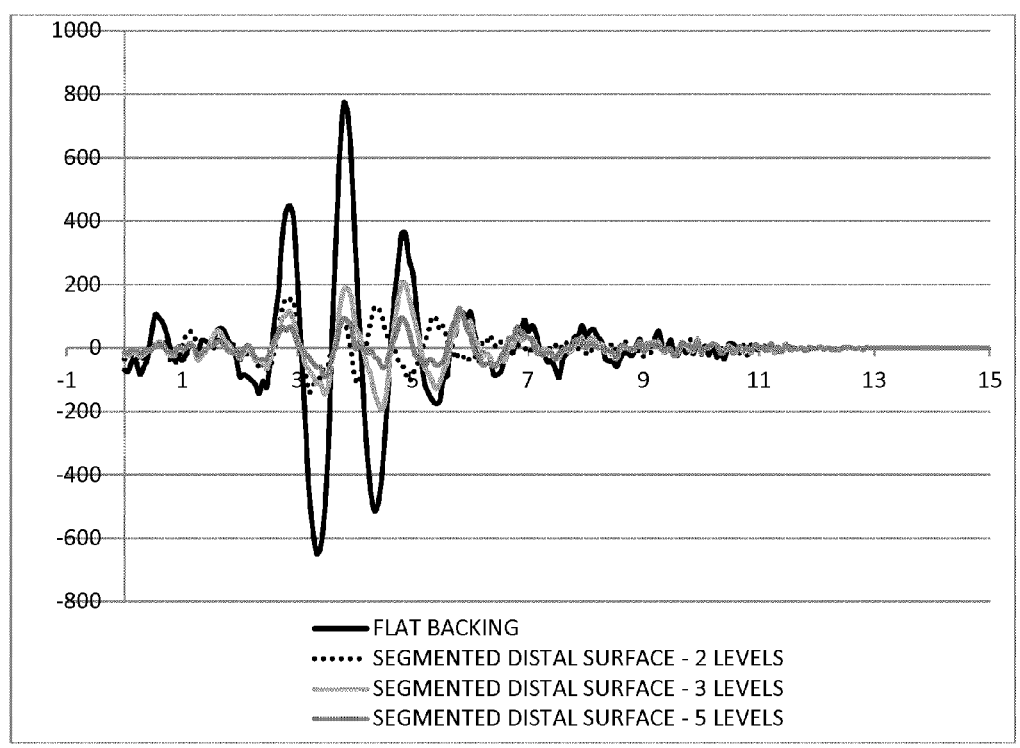
FIG. 7A shows simulated secondary signals produced by transducers with a flat backing and with various stepped segmented backings.

The simulated performance of cloned and segmented surfaces, relative to stepped surfaces, is illustrated in FIGS. 6A and 6B. In FIG. 7A, various secondary signal waveforms are shown that compare stepped segmented surfaces, such as the stepped surface shown in FIG. 5A, to the secondary signal obtained from a flat (control) surface, based on a realistic waveform with a short pulse envelope having a time duration of approximately three cycles. As can be seen from the Figure, the amplitude of the secondary signals is reduced, but remains appreciable, for all segmented surfaces, with the best performance obtained for the 5-level stepped segmented surface. The incomplete cancellation of the secondary waveform based on destructive interference can be understood to occur because of the rapid variations in the amplitude of the pulse waveform at the leading and trailing edges of the pulse. These contributions of these edges to the secondary signal are not cancelled due to the equal weighting of reflected components for all levels that arises from the common surface area of the levels.

Figure 7B:
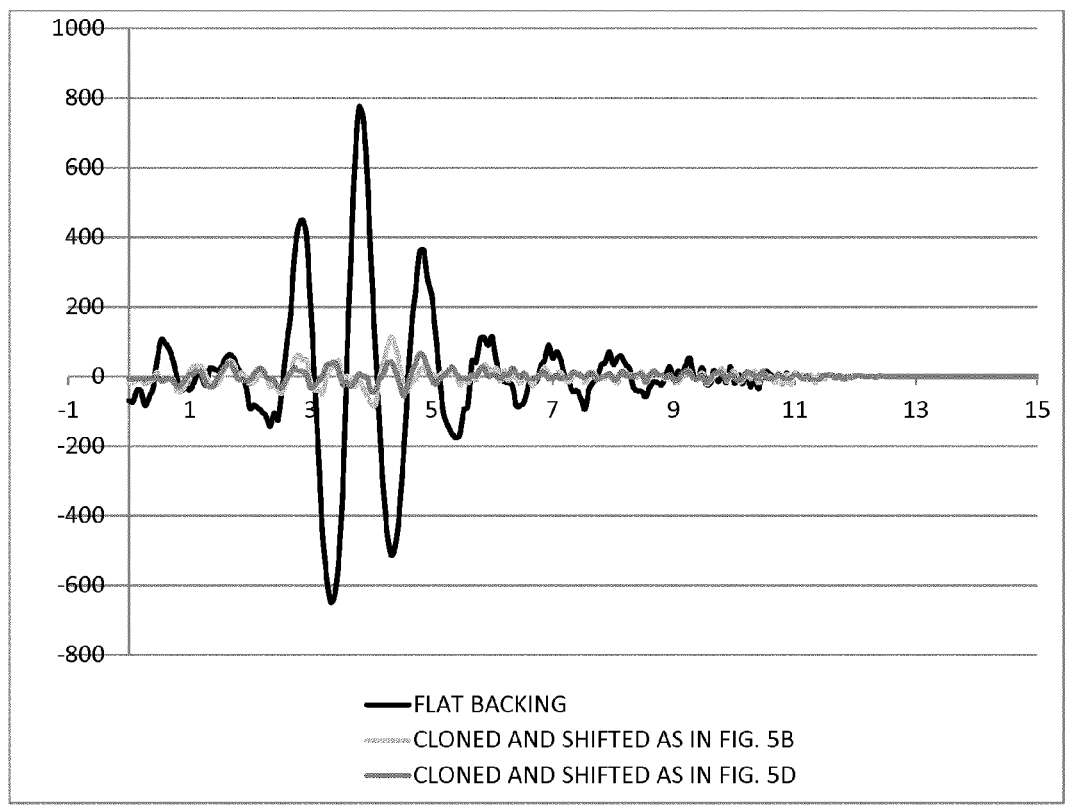
FIG. 7B shows simulated secondary signals produced by transducers with a flat backing and with various segmented backings defined by a clone and shift operation.

In contrast, FIG. 7B shows the improved cancellation that occurs for segmented surfaces that are defined by the cloning and shifting method described herein. The Figure shows the broad cancellation of the secondary signal obtained from segmented surfaces based on the single clone and shift surface of FIG. 5B, and the superset-based clone and shift operation shown in FIG. 5D.

FIG. 7B therefore shows that in the case of short pulses, the nulling of the secondary signal can be improved by defining a segmented surface according to the cloning and shifting method described above. However, it will be understood that a more general prescription may also be employed to obtain similar results. This more general prescription can be understood by examining the progression of the total surface area for the levels, which is shown in FIGS. 5E and 5G, which shown segmented surfaces that are functionally equivalent to the segmented surfaces shown in FIGS. 5D and 5F, respectively. The segmented surface shown in FIG. 5E is characterized by per-level surface areas that vary, in units of the surface area of the first level, as follows: 1 (L1), 3 (L2), 3 (L3) and 1 (L4). Similarly, the segmented surface shown in FIG. 5G is characterized by per-level surface areas that vary, in units of the surface area of the first level, as follows: 1 (L1), 4 (L2), 6 (L3), 4 (L4), and 1 (L5).

These segmented surfaces are characterized by per-level surface areas that monotonically increase to one or more intermediate levels, and then monotonically decrease. It is also apparent that for each level between the first level and the one or more intermediate levels, there exists an associated level with an approximately equal surface area that resides between the one or more intermediate levels and the final level.

Accordingly, one prescription for defining a segmented surface involves providing a segmented surface characterized by per-level surface areas that monotonically increase to one or more intermediate levels, and then monotonically decrease. The segmented surface may further be characterized such that for each level between the first level and the one or more intermediate levels, there exists an associated level with an approximately equal surface area that resides between the one or more intermediate levels and the final level. Although the example embodiments shown in the Figures illustrate segmented surfaces for which the per-level surface areas are related by a whole-number multiplier, it is understood that this is not a general requirement, and that in other embodiments, two or more of the per-level surface areas may be related by numbers other than whole numbers. As described above, the surface areas of the various levels may be defined to compensate for depth-dependent attenuation in order to achieve suitable interference of reflected acoustic waves.

Ultrasonic transducers, and backings for ultrasonic transducers as disclosed in the preceding embodiments, may be fabricated according to various processes. One example method for forming a segmented backing surface is to employ standard transducer processing equipment to segment the backing into several steps. These steps may be separated by transition walls as described above, and may be machined using equipment such as a dicing saw. The width of the steps can be controlled by the width of the blade and the index step of the dicing saw machine.

Other material removal processes are also conceived such as CNC machining or laser machining. The use of a 3, 4, or 5 axis CNC machine could be employed to provide transition walls that are more tapered in nature. Similarly, laser machining may be employed to control the wall profile, as the laser spot typically removes just a small amount of material per laser pulse and thus provides for fine control over the geometrical profile of the surface of the backing.

Although the images presented are for single element transducers, this technique can also be applied to annular, linear and phased arrays of 1 D, 1.25 D, 1.5 D, 1.75 D, and 2 D arrayed devices as well as well as sparsely populated arrays. FIG. 6 shows an example of an ultrasonic array 700 including an array of transducers 705, each having a backing having a further surface 710 that is segmented over at least a portion thereof (the Figure shows the example case of the further surface being the distal surface of the backing).

It will also be understood that the transducer stack design may also contain more than one active layer. The polarization of the active layers be polarized in the same orientation or in opposite orientation. Any transducer type that utilizes a backing layer can be modified according to the embodiments provided in the present disclosure to reduce or modify the effects of reverberation within the backing layer itself.

In some embodiments, the devices described herein may be employed as ultrasound transducers in minimally invasive ultrasound applications such as imaging and/or therapeutic catheters. Non-limiting examples of such minimally invasive ultrasound catheters having ultrasonic transducers that may be modified to include a segmented backing include those described in U.S. Pat. No. 8,460,195, titled "SCANNING MECHANISMS FOR IMAGING PROBE", and filed on Mar. 27, 2009, which is incorporated herein by reference in its entirety, and in Patent Cooperation Treaty Patent Application No. PCT/CA/2012/050057, as referenced above. Useful ultrasound frequencies for catheters typically lie in the 5-100 MHz range. The size of vessels where a catheter may be useful will result in catheters of approximately 2-15 French. Assuming a typical backing like conductive epoxy (with a speed of sound of 1950 m/s) and a reasonable number of segment levels to be in the range of 4-6 levels, then the stack thickness for a 10 MHz PZT transducer could be kept to within a total thickness of approximately 600 microns. The use of materials with a relatively slow speed of sound, such as rubber materials, having a speed of sound on the order of 1000-1500 m/s, would lead to minimum thicknesses of about 400 microns. Depending on the nature of the distal housing that holds the transducer inside the sheath of the catheter, a 60 MHz transducer of reasonable axial imaging capability could be assembled and realized inside an approximately 2 Fr catheter or smaller.

It will be understood that embodiments of the present disclosure that permit a reduction in the backing thickness may be employed in a wide variety of ultrasound applications in which limited space is available for the transducer. Such embodiments may be useful, for example, applications in which the ability to place an ultrasound transducer in close proximity to tissue allows for the use of higher frequency ultrasound to image the regions of interest for improved imaging resolution. Therefore intracardiac imaging, intravascular imaging, needle based and endoscopic applications such as bladder and other urethral imaging applications or auditory imaging applications can benefit from this disclosure respectively. Although many of the examples provided herein relate to medical ultrasonic transducers and medical applications involving ultrasonic transducers, such as ultrasonic imaging transducers and ultrasonic therapeutic devices, it will be understood that various embodiments of the present disclosure may be employed in other applications and fields. For example, ultrasonic transducers having segmented backing according to the preceding embodiments may be employed for applications such as no-contact sensing, motion sensors, flow sensing, non-destructive testing, range finding, location sensing, and communications. They can also be used to reduce the pulse duration of energy delivered during therapeutic ultrasound, such as High Intensity Focused Ultrasound (HIFU).

The following examples are presented to enable those skilled in the art to understand and to practice embodiments of the present disclosure. They should not be considered as a limitation on the scope of the disclosure, but merely as being illustrative and representative thereof.

EXAMPLES

Figure 8:
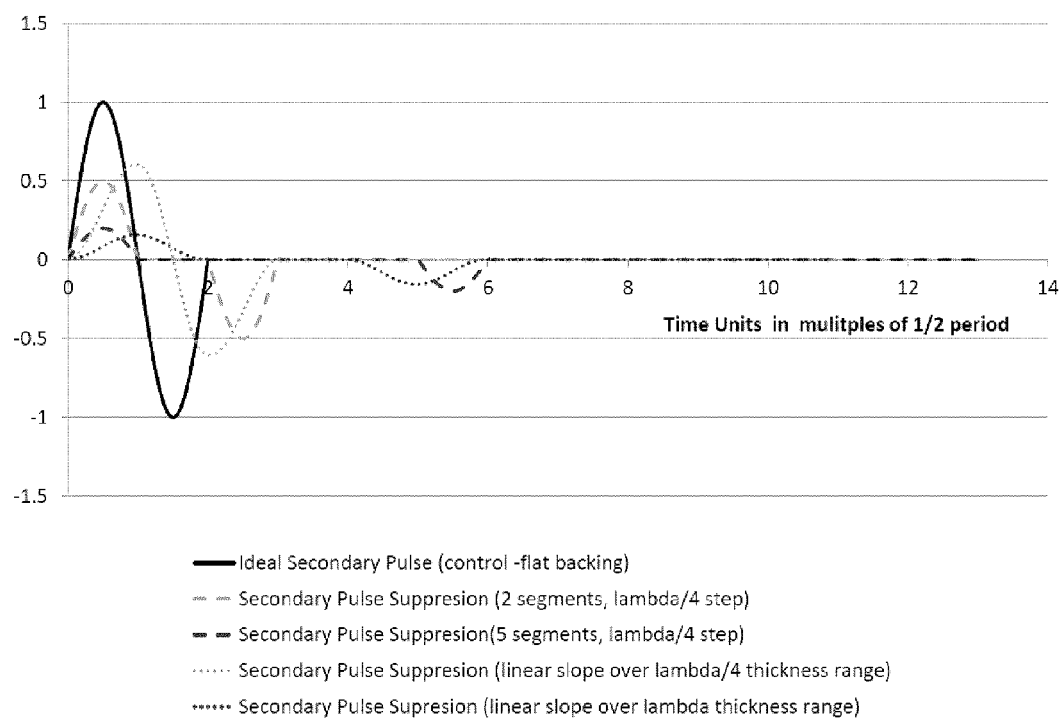
FIG. 8 plots simulated secondary signals that are produced by transducers with various segmented backing profiles, for the case of a simulated primary signal consisting of a single full cycle pulse.

Example 1: Modelling of Secondary Signal Produced by Reflection of Single Cycle Pulse A mathematical model was employed to demonstrate the effect of different segmented profiles on a primary signal consisting of a single cycle pulse. A number of different segmented profiles were modeled, and the resulting secondary signals are shown in FIG. 8. The model shows how various portions of the reflected pulse are removed via destructive interferences caused by the reflected waves, and how some residual portions of the reflected pulse that are not removed are decreased in amplitude due to the temporal spreading of the reflected pulse.

FIG. 8 shows four different secondary signals (the primary signal is not shown), corresponding to different profiles of the distal surface of the backing. The thick solid Black line shows the secondary signal that is produced by a backing of uniform thickness 'T'. This curve is merely a reproduction of the primary pulse. This secondary signal is referred to below as the "control" secondary signal.

The dashed light grey line shows the secondary signal obtained from a two-level segmented backing consisting of two segments of equal area, where the first segment is of thickness 'T' and the second is of thickness 'T+$\lambda$/4' where X is the wavelength of the center frequency of the acoustic wave propagating within the backing layer. The resulting secondary signal is a double pulse shape, where the pulses are ½ of the signal intensity of the control secondary signal obtained from the flat surface. The secondary signal in this example is extended in time by an extra ½ period. The two reflected acoustic waves that form the secondary signal are phase-shifted by 180 degrees, such that when one signal has a maximum positive intensity, the other signal has a maximum negative intensity and when summed, the portions of the signal that overlap cancel. The leading half wave section of the reflected signal from the shorter segment and the trailing half wave section of the reflected signal from the longer segment remain. They do not cancel and they are each ½ the intensity of the leading and trailing sections of the control secondary signal with a separation gap of ½ wavelength.

The dashed dark grey line shows the reflected signal from a backing of variable thickness where there are five segments of equal area where the first segment is of thickness 'T' and the additional four segments are each of and additional thickness equal to 'T+N($\lambda$/4)' where N=1 . . . 4 relative to the thinnest segment. This curve shows that increasing the number of segments results in a longer separation between the residual peaks, and increased attenuation of the residual peaks. The number of segments can be increased, to further minimize the peak intensity and to further lengthen the pulse duration of the secondary pulse, which may be done at the expense of increased fabrication complexity.

The dotted light grey line shows the secondary signal obtained for a transducer having a backing with a segmented distal surface having 21 segments, where the segments are each of additional thickness equal to 'T+N($\lambda$/80)', and where N=1 . . . 20 relative to the thinnest segment (for a total thickness variation of a quarter of a wavelength). This example segmented surface represents an approximation of a wedge shaped backing, where the backing is linearly increasing in thickness. While this approach provides the benefit of reducing the amplitude of the secondary signal via the spreading out of the secondary signal over an increased time duration, the amplitude of the secondary signal remains appreciable.

The dotted dark grey line shows the secondary signal obtained for a transducer having a backing with a segmented distal surface having 81 segments, where the segments are each of additional thickness equal to 'T+N($\lambda$/80)', and where N=1 . . . 80 relative to the thinnest segment (for a total thickness variation of one wavelength). The portions of the leading and trailing slopes that are not fully cancelled have partially spread. The peak of the residual rising and falling slopes are actually a little lower than the peaks from the segmented approach.

Figure 9:
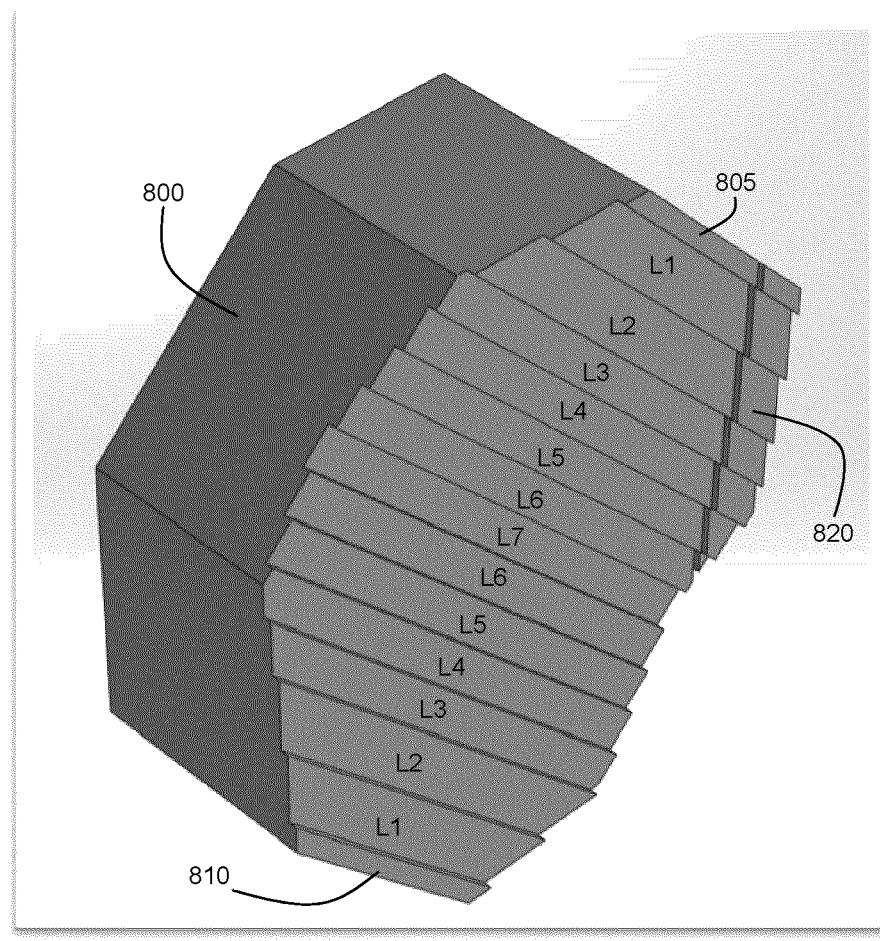
FIG. 9 shows a perspective view (from the bottom surface of the backing) of a single element transducer with a polygon aperture. PZT and matching layers are not shown.

Example 2: Mathematical Model and Experimental Demonstration of Suppression of Secondary Signal in Transducer Having Backing with Segmented Distal Surface In the present example design, a transducer with a segmented backing was fabricated, and the acoustic response was experimentally measured and mathematically modeled. FIG. 9 is an illustration of the segmented backing of the transducer design. As shown in the Figure, the example transducer is a single-element transducer with a polygonal aperture, having a backing layer 800 that is segmented into seven levels (L1-L7), where the areas of the various segments are equal. The active and matching layers are not shown in the Figure. The section 820 to the right of the dark band is not active. The distal surface of the backing layer includes the segmented surface define by the segments forming the seven levels L1-L7, and two additional base regions 805 and 810 of the backing at the upper and lower ends thereof. The thickness of the backing is thicker at the top and bottom of the device and thinnest in the middle.

A transducer stack, designed for a center frequency of 10 MHz, was fabricated with a 5H type PZT as the active layer, a 400 um layer of silver epoxy as the backing and silver epoxy and non-conductive epoxy as the respective matching layers. The backing of the transducer was then diced into segments as per FIG. 9, using a conventional dicing saw. Mounting the transducer into a fixture, the device could be placed in a water tank and excited with a single cycle transmit pulse. With a hydrophone the one-way waveform along the principle axis of the transducer could be measured. Two-way measurements measured off of a flat plastic surface were also taken.

A one-way signal (or response) is a signal that is the result of being converted through the active piezoelectric layer of the transducer once. For example: If a transmitted acoustic signal is detected from a transducer using an acoustic sensor such as a hydrophone, then the detected hydrophone signal is a one-way signal. A two-way signal (or response) is a signal that is the result of being converted through the active piezoelectric layer of the transducer twice. For example, when the same transducer is used to acoustically transmit an electric drive signal and then in turn is used to sense the reflected transmitted acoustic signal from the medium, then the detected electrical signal by the transducer is a two-way signal.

Figure 10A:
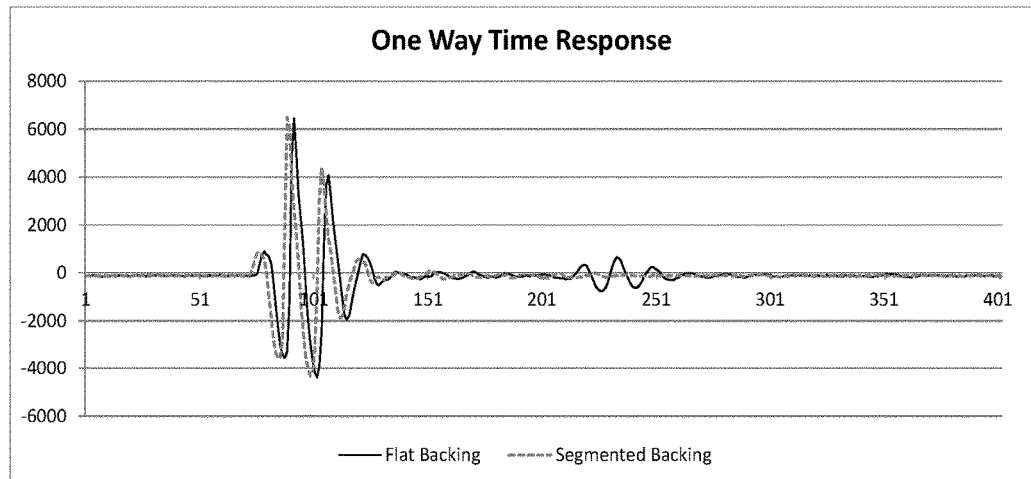
FIG. 10A plots the one-way measured time response of a transducer stack with a flat backing (solid line), relative to the same stack having a patterned segmented backing (dashed line) matching the pattern shown in FIG. 8.
Figure 10B:
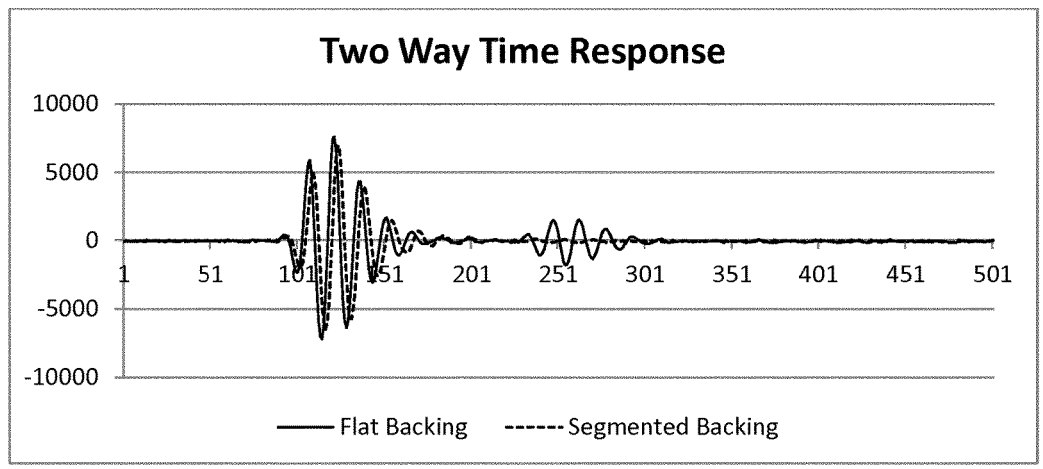
FIG. 10B plots the two-way measured time response of a transducer stack with a flat backing (solid line), relative to the same stack having a patterned segmented backing (dashed line) matching the pattern shown in FIG. 8.

The one-way and two-way measurements were obtained for the transducer prior to, and after, forming the segmented layer. The strength of the secondary signals with and without the segmented surface were compared, as shown in FIGS. 10A and 10B, respectively (the x-axis is in samples (with a sample period of 5 nsec—sampling rate of 200 MHz). The amplitude of the one-way signal was reduced by about 16.5 dB and the 2-way was reduced by about 20 dB.

Figure 11:
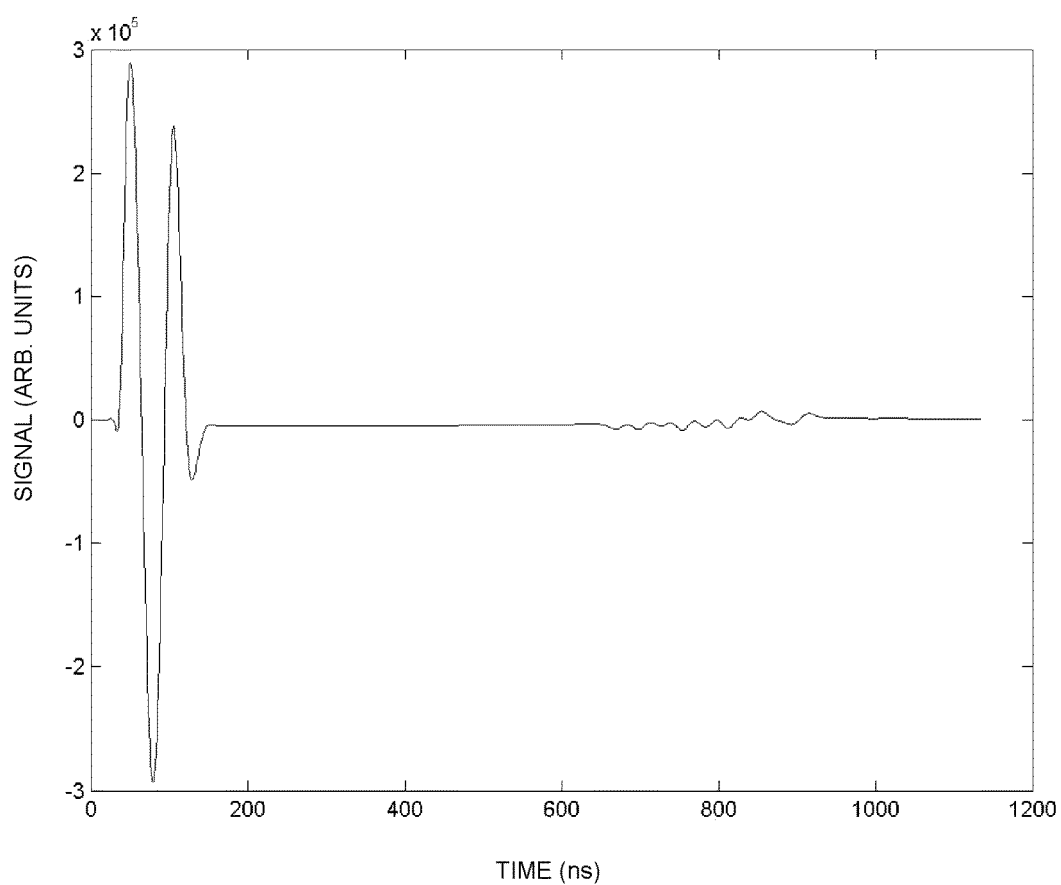
FIG. 11 is a simulated time response of the transmitted signal from the transducer stack design represented in FIG. 8, demonstrating a reduced secondary transmit signal for the segmented transducer backing relative to that obtained with a flat transducer backing.

A linear propagation model simulation tool (K-wave found at http://www.k-wave.org/index.php) was also employed to model the acoustic response of the transducer. The single element transducer was modeled with a 12.5 MHz center frequency, and the silver epoxy backing layer had a thickness of approximately 450 microns. The simulated primary signal used to drive the transducer was compared to the simulated reflected signal from a segmented patterned backing (the backing was generated in 3D CAD), providing simulated one-way results. The secondary pulses predicted by the mathematical model are shown in FIG. 3 (planar backing) and FIG. 11 (segmented backing). It was found that the transmitted electrical pressure of the secondary signal was reduced by approximately 19 dB when the segmented backing was employed.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An ultrasonic transducer comprising:
   an active layer; and
   a backing having a proximate surface that is proximate to said active layer, and a further surface therebelow, wherein at least a portion of said further surface is a segmented surface;
   wherein said segmented surface comprises a plurality of approximately planar segments, each segment being approximately parallel to said proximate surface;
   wherein at least two of the segments are spatially offset in a longitudinal direction that is approximately perpendicular to said proximate surface, thereby defining two or more levels of said segmented surface, such that each level has a different backing thickness associated therewith; and
   wherein the surface area associated with each level is provided to compensate for depth-dependent attenuation associated with propagation loss within the backing, thereby facilitating suitable interference of acoustic waves reflected from the segmented surface.

2. The ultrasonic transducer according to claim 1 wherein said ultrasonic transducer has dimensions that are sufficiently small for use within a minimally invasive catheter.

3. The ultrasonic transducer according to claim 1 wherein said ultrasonic transducer is a high frequency ultrasonic transducer.

4. The ultrasonic transducer according to claim 1 wherein at least three of the segments are spatially offset in the longitudinal direction, thereby defining three of more levels of said segmented surface.

5. The ultrasonic transducer according to claim 1 wherein said levels are spatially offset such that an internally propagating acoustic pulse incident upon said segmented surface is reflected towards said active layer with a temporally stretched pulse profile, thereby reducing the amplitude of excitations of said active layer upon subsequent transmission through said active layer.

6. The ultrasonic transducer according to claim 1 wherein each level has associated therewith a surface area defined by the sum of the surface areas of the segments forming the level, and wherein neighbouring levels are separated by a distance equaling approximately an odd multiple of a quarter an operational wavelength associated with the ultrasonic transducer, such that acoustic waves reflected from neighbouring levels are out of phase upon subsequent transmission through said active layer, thereby reducing the amplitude of excitations in said active layer.

7. The ultrasonic transducer according to claim 6 wherein the surface areas of the levels are selected such that the reflected acoustic power from all odd levels approximately equals reflected acoustic power from all even levels.

8. The ultrasonic transducer according to claim 6 wherein the surface areas of the levels are selected such that the total surface area of all odd levels approximately equals the total surface area of all even levels.

9. The ultrasonic transducer according to claim 6 wherein the surface areas of said levels are approximately equal.

10. The ultrasonic transducer according to claim 6 wherein at least one pair of adjacent levels are separated by a distance equaling approximately a quarter of an operational wavelength associated with the ultrasonic transducer.

11. The ultrasonic transducer according to claim 6 wherein said segments are configured such that the thickness of said backing varies in one lateral dimension.

12. The ultrasonic transducer according to claim 6 wherein said segments are configured such that the thickness of said backing varies in two lateral dimensions.

13. The ultrasonic transducer according to claim 11 wherein said segments are arranged such that the thickness varies monotonically along one lateral dimension.

14. The ultrasonic transducer according to claim 6 wherein at least one level comprises two or more segments that are laterally offset from one another, while having a common backing thickness associated therewith.

15. The ultrasonic transducer according to claim 6 wherein the surface areas of said levels are configured to reduce the amplitude of excitations of said active layer that result from a short primary pulse having a duration of approximately 1 cycle to 3 three cycles.

16. The ultrasonic transducer according to claim 6 wherein the surface areas of the levels of increase monotonically from a first level to one or more intermediate levels having a common surface area, and then decrease monotonically to a final level.

17. The ultrasonic transducer according to claim 16 wherein, for each level between said first level and said one or more intermediate levels of said segmented surface, there exists an associated level with an approximately equal surface area that resides between said one or more intermediate levels and said final level.

18. The ultrasonic transducer according to claim 17 wherein the surface area of each level is related to the surface area of said first level by a multiplier that approximately equals a whole number.

19. The ultrasonic transducer according to claim 6 wherein said operational wavelength is approximately equal to a fundamental resonant wavelength.

20. The ultrasonic transducer according to claim 1 wherein a minimum thickness of said backing is sufficiently thick such that a primary acoustic wave does not overlap with the reflected acoustic waves within said active layer.

21. The ultrasonic transducer according to claim 1 wherein said further surface is an internal surface formed between a first layer of said backing and a second layer of said backing, wherein said first layer of said backing has an acoustic impedance that differs from that of said layer of said backing.

22. An ultrasonic transducer array comprising a plurality of ultrasonic transducers according to claim 1.

23. An ultrasonic transducer comprising:
   an active layer; and
   a backing having a proximate surface that is proximate to said active layer, and a further surface therebelow, wherein at least a portion of said further surface is a segmented surface;
   wherein said segmented surface comprises a plurality of approximately planar segments, each segment being approximately parallel to said proximate surface;
   wherein at least two of the segments are spatially offset in a longitudinal direction that is approximately perpendicular to said proximate surface, thereby defining two or more levels of said segmented surface, such that each level has a different backing thickness associated therewith; and
   wherein said further surface is an internal surface formed between a first layer of said backing and a second layer of said backing, wherein said first layer of said backing has an acoustic impedance that differs from that of said layer of said backing.

* * * * *